US006329516B1

(12) United States Patent
Halling et al.

(10) Patent No.: US 6,329,516 B1
(45) Date of Patent: Dec. 11, 2001

(54) LEPIDOPTERAN GABA-GATED CHLORIDE CHANNELS

(75) Inventors: Blaik P. Halling, Newtown, PA (US); Debra A. Yuhas, Wrightstown, NJ (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 09/002,361

(22) Filed: Jan. 2, 1998

Related U.S. Application Data

(60) Provisional application No. 60/044,976, filed on Apr. 28, 1997.

(51) Int. Cl.[7] .................................................. C07H 21/04
(52) U.S. Cl. .......................................... 536/23.5; 530/350
(58) Field of Search ........................... 530/350; 536/23.5; 435/320.1, 69.1

(56) References Cited

U.S. PATENT DOCUMENTS 5,767,261 * 6/1998 Wingate et al. ..................... 536/23.5

FOREIGN PATENT DOCUMENTS

WO 93/07161 * 4/1993 (WO) .

OTHER PUBLICATIONS

Anthony, N. M., et al., *Comparative Molecular Neurobiology*, Ed. by Y. Pichon, Birkhauser Verlag, Basel Switzerland (1993).
Bloomquist, J. R. *Ann Rev. Entomol.* 41: 163–190 (1996).
Cole, L. M., et al., *Life Sciences* 56: 757–765 (1995).
Darlison, M. G. *Trends of Neur. Sci.* 15: 469–474 (1992).
Daugherty, B.L., et al., *DNA Cell Biol.* 9: 453–459 (1990).
Eisenberg, D., et al., *Proc. Natl. Acad. Sci. USA* 81: 140–144 (1984).
Freissmuth, M., et al., *Proc Natl. Acad. Sci. USA* 88:8548–8552 (1991).
Ffrench–Constant, R. H. *Insect Biochem. Molec. Biol* 24: 335–345 (1994).
Ffrench–Constant, R. H. *Experimentia Supplementum* 63: 210–223 (1993).
Ffrench–Constant, R. H. *Nature* 363: 449–451 (1993).
Ffrench–Constant, R. H., et al., *Proc. Natl. Acad. Sci. USA* 88: 7209–7213 (1991).
Frohman, M. A., et al., *Proc. Natl. Acad. Sci. USA* 85: 8998–9002 (1988).
von Heijne, G., et al., *FEBS Letters* 244: 439–446 (1989).
von Heijne, G. *J. Membr. Biol.* 115: 195–201 (1990).
Henderson, J. E., et al. *Biochem. Biophys. Res. Commun.* 193: 474–482 (1993).
Herzog, H., et al. *DNA Cell Biol.* 13: 1221–1225 (1994).
Hosie, A. M., et al. *Brit. J. Pharmacol.* 115: 909–912 (1995).
Hosie, A. M., et al. *Brain Res.* 693: 257–260 (1995).
Kaku, K., et al. *Comp. Biochem. Physiol.* 108: 367–376 (1994).
Krishnaswamy, S., et al. *J. Biol. Chem.* 267: 26110–26120 (1992).
Lee, H–J., et al. *FEBS Letters* 335: 315–318 (1993).
Loh, E. Y. *Science* 243: 217 (1989).
Miyazaki, M., et al., *Comp. Biochem. Physiol.* 111B: 399–406 (1995).
Ohta, Y., et al., *Biochemistry* 31: 12680–12687 (1992).
Roux, K. H., et al., *BioTechniques* 8: 48–57 (1990).
Sieghart, W. *Pharmacol. Reviews* 47: 181–234 (1995).
Shotkoski, F. *FEBS Letters* 80: 257–262 (1996).
Thompson, M., et al., *Insect Mol. Biol.* 2: 149–154 (1993).
Thompson, M., et al., *FEBS Letters* 325: 187–190 (1993).
Ffrench–Constant, R.H. et al., GenBank Accession No. M69057 Dated Apr. 26, 1993.
Henderson, J.E. et al., GenBank Accession No. L17436 Dated Jul. 26, 1993.
Thompson, M. et al., GenBank Accession No. U28803 Dated Jun. 28, 1995.

* cited by examiner

*Primary Examiner*—Lorraine Spector
*Assistant Examiner*—Eileen B. O'Hara
(74) *Attorney, Agent, or Firm*—FMC Corporation

(57) ABSTRACT

Provided, among other things, is an isolated nucleic acid encoding a GABA-gated chloride channel having: (a) a nucleic acid including a sequence encoding a protein sequence of SEQ ID NO: 3, SEQ ID NO: 6 or SEQ ID NO: 8, or a sequence having at least about 85% sequence identity with SEQ ID NO: 3, SEQ ID NO: 6 or SEQ ID NO: 8, or (b) a nucleic acid that hybridizes with a nucleic acid encoding a protein sequence of SEQ ID NO: 3, SEQ ID NO: 6 or SEQ ID NO: 8 or the complementary sequence to SEQ ID NO: 3, SEQ ID NO: 6 or SEQ ID NO: 8, under stringent conditions; or (c) a nucleic acid that hybridizes with a nucleic acid having a sequence of SEQ ID NO: 1, SEQ ID NO: 4 or SEQ ID NO: 7 or the complementary sequence to SEQ ID NO: 1, SEQ ID NO: 4 or SEQ ID NO: 7, under stringent conditions; or (d) a nucleic acid has at least about 85% sequence identity with the coding region of SEQ ID NO: 1, SEQ ID NO: 4 or SEQ ID NO: 7.

6 Claims, 3 Drawing Sheets

```
cttgacgcct gagggnctgt aagaacacgc cagtcccgcc ggcaggctga tacgcggctg      60
ccggcagcca gcgtccgcaa gggcgcacgc ggacctgcaa aacATGCATA CGAGCCGTCC     120
                                            MetHisT hrSerArgPr
GCGCGGCGTG CACAGCATCG CGCTAGTGCT GTCTCTCGCG ATTGCCTGGT TACCTCATGC     180
oArgGlyVal HisSerIleA laLeuValLe uSerLeuAla IleAlaTrpL euProHisAl
TGACCATGCC GCGGGAGCGG GAGGAGGGGG GATGTTTGGT GACGTCAATA TCTCAGCCAT     240
aAspHisAla  A   G   A   G    G   G   G    M   F   G    D   V   N    I    S   A   I
TTTGGATTCG CTAAGTGTAA GCTACGACAA AAGAGTGAGG CCGAACTATG GAGGACCGCC     300
 L   D   S    L   S   V   S    Y   D   K    R   V   R    P   N   Y   G    G   P   P
AGTGGATGTG GGAGTCACCA TGTACGTGCT CTCCATCAGC TCCTTATCTG AAGTGAAAAT     360
 V   D   V    G   V   T   M    Y   V   L    S   I   S    S   L   S   E    V   K   M
GGATTTCACC CTGGATTTCT ACTTCAGACA ATTTTGGACA GACCCCAGGC TTGCTTACAA     420
 D   F   T    L   D   F   Y    F   R   Q    F   W   T    D   P   R    L    A   Y   K
AAAAAGGACG GGTGTGGAGA CTCTGTCCGT CGGCTCGGAA TTTATTAGAA ACATATGGGT     480
 K   R   T    G   V   E   T    L   S   V    G   S   E    F   I   R   N    I   W   V
ACCCGACACC TTCTTTGTTA ACGAAAAACA GTCTTATTTC CACATAGCTA CTACAAGCAA     540
 P   D   T    F   F   V   N    E   K   Q    S   Y   F    H   I   A   T    T   S   N
CGAATTCATA CGCATTCATC ATTCTGGATC TATTACTAGG AGTATAAGAC TGACTATCAC     600
 E   F   I    R   I   H   H    S   G   S    I   T   R    S   I   R   L    T   I   T
CGCTTCTTGT CCGATGGATT TGCAGTATTT TCCGATGGAC CGTCAATTAT GCAATATTGA     660
 A   S   C    P   M   D   L    Q   Y   F    P   M   D    R   Q   L   C    N   I   E
AATCGAAAGT TTTGGCTACA CCATGCGGGA CATCCGATAC AAGTGGAATG AGGGGCCCAA     720
 I   E   S    F   G   Y   T    M   R   D    I   R   Y    K   W   N   E    G   P   N
CTCAGTGGGT GTGTCGAGCG AAGTGTCTTT GCCGCAATTC AAGGTGCTGG CCACCGGCA     780
 S   V   G    V   S   S   E    V   S   L    P   Q   F    K   V   L   G    H   R   Q
GCGGGCCATG GAGATTTCTC TTACGACAGG AAACTACTCT CGTCTGGCAT GTGAAATTCA     840
 R   A   M    E   I   S   L    T   T   G    N   Y   S    R   L   A   C    E   I   Q
ATTTGTACGC TCGATGGGAT ACTATTTAAT TCAGATTTAT ATTCCGTCTG GCCTAATTGT     900
 F   V   R    S   M   G   Y    Y   L   I    Q   I   Y    I   P   S   G    L   I   V
CATTATATCT TGGGTATCAT TTTGGTTGAA TCGAATGCG ACACCTGCAA GGGTATCACT     960
 I   I   S    W   V   S   F    W   L   N    R   N   A    T   P   A   R    V   S   L
AGGTGTCACA ACTGTATTGA CGATGACGAC GCTCATGTCG TCCACGAATG CGGCTCTGCC    1020
 G   V   T    T   V   L   T    M   T   T    L   M   S    T   N   A    L    P
CAAGATCTCA TATGTCAAGT CCATCGATGT CTATCTGGGA ACTTGTTTCG TCATGGTCTT    1080
 K   I   S    Y   V   K   S    I   D   V    Y   L   G    T   C   F    V    M   V   F
CGCCAGTTTA CTAGAATATG CCACGGTTGG CTATATGGCT AAAAGGATAC AGATGAGGAA    1140
 A   S   L    L   E   Y   A    T   V   G    Y   M   A    K   R   I    Q    M   R   K
ACAAAGATTC ACTGCTGTTC AAAAAATGGC CGCCGAGAAG AAAATGCAAA TAGATGGTCC    1200
 Q   R   F    T   A   V   Q    K   M   A    E   K   K    M   Q   I    D    G   P
TCCAGGGTCA GCTGAGCCTA TCCCCCCACC GAGGACCAGC ACCCTATCTA GGCCACCACC    1260
 P   G   S    A   E   P   I    P   P   P    R   T   S    T   L   S    R    P   P   P
ACCTAGCCGA TTATCGGAGG TTCGGTTCAA AGTTCACGAT CCGAAGGCAT ATTCTAAAGG    1320
 P   S   R    L   S   E   V    R   F   K    V   H   D    P   K   A    Y    S   K   G
CGGTACTTTA GAAAACACTA TCAATGGGGC TCGGGGCCCA GCCCCAGGAC CTGCTCCACC    1380
 G   T   L    E   N   T   I    N   G   A    R   G   P    A   P   G    P    A   P   P
GGCAGACGAA GAAGCTGGAC CACCTCCGCA TCTCGTTCAT GCTTCCAAGG GTATCAACAA    1440
 A   D   E    E   A   G   P    P   P   H    L   V   H    A   S   K    G    I   N   K
ACTGCTGGGC ACGACCCCCT CGGACATCGA CAAGTACTCG CGCATCGTGT TCCCCGTCTG    1500
 L   L   G    T   T   P   S    D   I   D    K   Y   S    R   I   V    F    P   V   C
CTTCGTTTGC TTTAACCTTA TGTACTGGAT CATTTACCTT CACGTGTCTG ACGTCGTGGC    1560
 F   V   C    F   N   L   M    Y   W   I    I   Y   L    H   V   S    D    V   V   A
TGATGACTTG GTACTACTAG GCGAAGAAAA TTGAattctc tttaactata ccggacttgt    1620
 D   D   L    V   L   L   G    E   E   N    .
tttaacttag ggtgcttatg atcaaccatc catcaagttt cggtaaagtt ctttaaatcc    1680
tagaaacgct cagtaaaata atagcgttct tgtgtttat aaatataatt atagtacaga    1740
tcactatgtt tattatagat aagtgtcgtg tatattggca ctggtaatat taattcttta    1800
gaaaataaag ataatatgaa gttcaaaaaa aaaaaaaaaa aaaa                      1844
```

FIGURE 1

```
CGCCCCCGCT  CCGCGCCGCT  GCTGCTGGCG  CTCGCGGCCG  CCTTCCTACC  GCAAGCCAAC    60
ArgProArgS  erAlaProLe  uLeuLeuAla  LeuAlaAlaA  laPheLeuPr  oGlnAlaAsn
CATGTCGCGG  GTGCCGGTGG  GGGAGGGATG  TTCGGTGACG  TCAATATATC  AGCCATTTTG   120
HisValA  G     A  G  G     G  G  M     F  G  D  V     N  I  S     A  I  L
GATTCATTTA  GTATAAGTTA  CGACAAAAGA  GTAAGACCAA  ACTATGGAGG  TCCGCCAGTG   180
D  S  F  S     I  S  Y     D  K  R     V  R  P  N     Y  G     G  P  V
GAGGTGGGCG  TCACCATGTA  TGTGCTCTCT  ATCAGCTCCG  TCTCCAAGT   GCTCATGGAT   240
E  V  G  V     T  M  Y     V  L  S     I  S  S  V     S  E  V     L  M  D
TTCACATTGG  ACTTTTACTT  CAGACAATTT  TGGACTGATC  CTCGATTAGC  ATACAAAAAA   300
F  T  L  D     F  Y  F     R  Q  F     W  T  D  P     R  L  A     Y  K  K
AGAACCGGAG  TTGAAACTTT  ATCTGTGGGC  TCAGAATTCA  TAAAGAACAT  ATGGGTACCC   360
R  T  G  V     E  T  L     S  V  G     S  E  F  I     K  N  I     W  V  P
GACACGTTCT  TTGTAAATGA  AAAGCAATCT  TATTTCCATA  TAGCAACAAC  CAGCAATGAA   420
D  T  F  F     V  N  E     K  Q  S     Y  F  H  I     A  T  T     S  N  E
TTCATCCGTA  TACACTATTC  TGGCTCTATC  ACTAGAAGTA  TCAGATTGAC  GATCACAGCC   480
F  I  R  I     H  Y  S     G  S  I     T  R  S  I     R  L  T     I  T  A
TCTTGCCCGA  TGAATTTGCA  ATACTTCCCG  ATGGATCGAC  AGTTGTGCCA  CATAGAAATT   540
S  C  P  M     N  L  Q     Y  F  P     M  D  R  Q     L  C  H     I  E  I
GAAAGTTTCG  GCTACACCAT  GCGGGACATC  AGATACAAAT  GGAACGAAGG  GCCCAACTCT   600
E  S  F  G     Y  T  M     R  D  I     R  Y  K  W     N  E  G     P  N  S
GTGGGTGTTT  CCAGCGAAGT  GTCGCTGCCG  CAGTTCAAGG  TGCTGGGTCA  TCGCCAACGA   660
V  G  V  S     S  E  V     S  L  P     Q  F  K  V     L  G  H     R  Q  R
GCTATGGAGA  TCTCCCTTAC  TACAGGAAAT  TATTCACGGT  TGGCATGTGA  AATACAATTC   720
A  M  E  I     S  L  T     T  G  N     Y  S  R  L     A  C  E     I  Q  F
GTTCGGTCTA  TGGGATATTA  CTTAATCCAA  ATTTATATTC  CCTCTGGTTT  GATTGTCATC   780
V  R  S  M     G  Y  Y     L  I  Q     I  Y  I  P     S  G  L     I  V  I
ATATCATGGG  TATCATTTTG  GTTGAATCGA  AATGCCACAC  CAGCTCGAGT  GGCCCTAGGT   840
I  S  W  V     S  F  W     L  N  R     N  A  T  P     A  R  V     A  L  G
GTTACCACTG  TATTGACAAT  GACAACGCTT  ATGTCGTCTA  CTAACGCGGC  GCTGCCCAAG   900
V  T  T  V     L  T  M     T  T  L     M  S  S  T     N  A  A     L  P  K
ATCTCATACG  TCAAATCCAT  AGATGTATAT  CTGGGACAT   GTTTCGTCAT  GGTATTCGCT   960
I  S  Y  V     K  S  I     D  V  Y     L  G  T  C     F  V  M     V  F  A
AGTCTACTAG  AATACGCGAC  TGTGGGATAT  ATGGCAAAGA  GAATACAGAT  GAGAAAACAA  1020
S  L  L  E     Y  A  T     V  G  Y     M  A  K  R     I  Q  M     R  K  Q
AGATTTGTGG  CCATACAGAA  AATAGCTTCT  GAAAAGAAAA  TCCCCGTTGA  CTGCCCACCC  1080
R  F  V  A     I  Q  K     I  A  S     E  K  K  I     P  V  D     C  P  P
GTAGGCGATC  CACATACTTT  ATCGAAGATG  GGAACACTTG  GCAGATGCCC  ACCCGGTAGA  1140
V  G  D  P     H  T  L     S  K  M     G  T  L  G     R  C  P     P  G  R
CCATCGGAGG  TGCGGTTCAA  AGTGCATGAC  CCAAAAGCGC  ATTCCAAAGG  CGGGACGTTA  1200
P  S  E  V     R  F  K     V  H  D     P  K  A  H     S  K  G     G  T  L
GAGAACACTA  TTAATGGAGG  TCGCAGTGGA  GCAGAAGAAG  AAAACCCAGG  CCCGCCCCCA  1260
E  N  T  I     N  G  G     R  S  G     A  E  E  E     N  P  G     P  P  P
CACATTTTAC  ATCCCGGCAA  GGACATAAGC  AAACTGCTCG  GCATGACTCC  CTCGGACATC  1320
H  I  L  H     P  G  K     D  I  S     K  L  L  G     M  T  P     S  D  I
GACAAGTACT  CGCGCATCGT  GTTCCCCGTC  TGCTTCGTTT  GCTTTAACCT  TATGTACTGG  1380
D  K  Y  S     R  I  V     F  P  V     C  F  V  C     F  N  L     M  Y  W
ATCATTTACC  TTCACGTGTC  TGACGTCGTG  GCTGACGATC  TGGTTCTACT  GGAAGAGGAT  1440
I  I  Y  L     H  V  S     D  V  V     A  D  D  L     V  L  L     E  E  D
AAATAGaggg  cgcagtacat  aatccactta  ttttccacaw  ctgcaagcta  aataataatt  1500
K  .
tgaaacggat  aaaacttta                                                   1519
```

FIGURE 2

```
C TTC GTG AAC GAA AAG CAA TCG TAC TTC CAC ACG GCC ACC ACC AGT AAT        49
  Phe Val Asn Glu Lys Gln Ser Tyr Phe His Thr Ala Thr Thr Ser Asn
    1           5                   10                  15

GAG TTC ATC CGC ATC CAC CAC TCG GGC TCC ATC ACG CGT AGC ATA AGG          97
Glu Phe Ile Arg Ile His His Ser Gly Ser Ile Thr Arg Ser Ile Arg
            20                  25                  30

CTC ACC ATC ACG GCC TCC TGC CCC ATG AAC CTG CAG TAC TTC CCC ATG         145
Leu Thr Ile Thr Ala Ser Cys Pro Met Asn Leu Gln Tyr Phe Pro Met
        35                  40                  45

GAT CGG CAG CTG TGC CAC ATC GAG ATC GAG AGT TTC GGC TAC ACC ATG         193
Asp Arg Gln Leu Cys His Ile Glu Ile Glu Ser Phe Gly Tyr Thr Met
    50                  55                  60

CGG GAC ATC CGG TAC AAA TGG AAC GAG GGG NCC AAC TCG GTG GGC GTT         241
Arg Asp Ile Arg Tyr Lys Trp Asn Glu Gly Xaa Asn Ser Val Gly Val
65                  70                  75                  80

TCA AAC GAA GTG TCG CTA CCG CAG TTC AAG GTG TTG GGC CAT CGT CAA         289
Ser Asn Glu Val Ser Leu Pro Gln Phe Lys Val Leu Gly His Arg Gln
                85                  90                  95

CGT GCC ATG GAA ATA TCG CTC ACA ACA GGA AAC TAC TCC CGG CTG GCG         337
Arg Ala Met Glu Ile Ser Leu Thr Thr Gly Asn Tyr Ser Arg Leu Ala
            100                 105                 110

TGC GAG ATC CAG TTC GTG CGC TCG ATG GGC TAC TAC CTG ATC CAG ATC         385
Cys Glu Ile Gln Phe Val Arg Ser Met Gly Tyr Tyr Leu Ile Gln Ile
        115                 120                 125

TAC ATA CCA TCC GGC CTC ATC GTC ATA ATA TCG TGG GTG TCT TTC TGG         433
Tyr Ile Pro Ser Gly Leu Ile Val Ile Ile Ser Trp Val Ser Phe Trp
    130                 135                 140

TTG AAC CGC AAC GCG ACG CCG GCG CGC GTG CAG CTG GGC GTC ACC ACC         481
Leu Asn Arg Asn Ala Thr Pro Ala Arg Val Gln Leu Gly Val Thr Thr
145                 150                 155                 160

GTG CTC ACC ATG ACC ACG CTC ATG TCT TCC ACT AAT GCG GCG CTG CCG         529
Val Leu Thr Met Thr Thr Leu Met Ser Ser Thr Asn Ala Ala Leu Pro
                165                 170                 175

AAG ATC TCG TAC GTT AAG TCC ATC GAT GTG TAC CTC GGC ACC TGC TTC         577
Lys Ile Ser Tyr Val Lys Ser Ile Asp Val Tyr Leu Gly Thr Cys Phe
            180                 185                 190

GTT ATG GTG TTC ACC AGT CTG CTA GAG TAC GCG ACG GTG GGG TAT ATG         625
Val Met Val Phe Thr Ser Leu Leu Glu Tyr Ala Thr Val Gly Tyr Met
        195                 200                 205

TCG AAG AGA ATA CAG ATG AGA AAG CAG CGC TTT GTC GCG ATC CC              669
Ser Lys Arg Ile Gln Met Arg Lys Gln Arg Phe Val Ala Ile
    210                 215                 220
```

FIGURE 3

LEPIDOPTERAN GABA-GATED CHLORIDE CHANNELS

This is a nonprovisional of application Ser. No. 60/044,976, filed Apr. 28, 1997.

The present invention relates to GABA-gated chloride channels from insects of the order lepidoptera, which are butterflies, moths and skippers that as adults have four broad or lanceolate wings.

Gamma amino butyric acid (GABA) is the major inhibitory neurotransmitter in the insect CNS and periphery; modulating membrane potential through a GABA-gated chloride channel (Anthony et al., *GABA receptor molecules of insects,* Y. Pichon, ed., Birkhauser Verlag, Basel, Switzerland, 1993; Bloomquist, *Ann. Rev. Entomol.* 41: 163–190, 1996; Hosie et al., *Brit. J. Pharmacol.* 115: 909–912, 1995). The significance of this GABA-gated channel (i.e., GABA receptor) as the site of action for a number of commercial insecticides has been known since the 1960s, but attempts to isolate the gene have been frustrated by the low homology between the insect sequence and available vertebrate probes and a low transcript abundance (Darlison, *Trends in Neur. Sci.* 15: 469–474, 1992; ffrench-Constant, *Insect Biochem. Molec. Biol.* 24: 335–345, 1994). More recently, a series of studies, directed by R. ffrench-Constant, utilized a conventional genetic approach that successfully located the gene (rdl) that determines resistance to dieldrin on the Drosophila polytene chromosome map (ffrench-Constant, *Experimentia Supplementum.* 63: 210–223, 1993; ffrench-Constant et al., *Nature* 363: 449–451, 1993). Isolation and expression of Drosophila rdl has established its function as a GABA-gated chloride channel, though it has less than 35% homology to any of the subunits which constitute the functional analogue in vertebrates.

Isolation of the Drosophila sequence has since been followed by full-length determinations of rdl-like GABA receptors from the mosquito *Aedes aegypti* as well as partial sequences from the flour beetle and a roach (Kaku and Matsumura, *Comparative Biochemistry and Physiology C Pharmacology Toxicology and Endocrinology* 108: 367–376, 1994; Miyazaki et al., *Comparative Biochemistry and Physiology* 111, 399–406, 1995; Thompson et al., *Insect Mol. Biol.* 2: 149–154, 1993; Thompson et al., *FEBS Letters* 325: 187–190, 1993). These gene determinations have allowed analyses to be conducted across several orders of insects showing that many species have adopted the same apparent strategy for developing resistance to insecticides that act at the chloride channel; mutation of a critical alanine in the second transmembrane domain to a serine. Indeed, site-directed mutagenesis experiments in heterologous expression systems have shown that altering this single residue is sufficient to reduce insecticidal potency by three orders of magnitude (Cole et al., *Life Sciences* 56: 757–765, 1995; Hosie et al., *Brain Res.* 693: 257–260, 1995; Lee et al., *FEBS Letters* 335: 351–318, 1993; Shotkoski et al., *FEBS Lett.* 80: 257–262, 1996). One of the more intriguing questions raised by the studies of resistance is why the mutation occurs at a low, but significant frequency in naive populations or in populations which have not been subjected to insecticide selection pressure in decades (ffrench-Constant, 1994).

Described herein are two lepidopteran receptor isoforms. In particular, these isoforms were isolated from the tobacco budwormn (TBW) *Heliothis virescens.* One isoform, TBW-a3 has in the second transmembrane the motif ProAlaArgVal<u>Ala</u>Leu (or PARVAL) usually associated with dieldrin susceptibility, while the other, TBW-a2, has the motif ProAlaArgVal$^{285}$<u>Ser</u>Leu (PARVSL, numbered as in SEQ ID 4) usually associated with dieldrin resistance. Genomic analysis reveals that both isoforms occur simultaneously in the same insecticide susceptible animals. Also described herein is a receptor isoform, TBW-a1, that has an unprecedented motif of ProAlaArgVal<u>Gln</u>Leu (or PARVQL).

SUMMARY OF THE INVENTION

In a first embodiment, the invention provides an isolated nucleic acid encoding a GABA-gated chloride channel comprising:

(a) a nucleic acid including a sequence encoding a protein sequence of SEQ ID NO: 3, SEQ ID NO: 6 or SEQ ID NO: 8, or a sequence having at least about 85% sequence identity with SEQ ID NO: 3, SEQ ID NO: 6 or SEQ ID NO: 8; or (b) a nucleic acid that hybridizes with a nucleic acid encoding a protein sequence of SEQ ID NO: 3, SEQ ID NO: 6 or SEQ ID NO: 8 or the complementary sequence to SEQ ID NO: 3, SEQ ID NO: 6 or SEQ ID NO: 8, under stringent conditions; or (c) a nucleic acid that hybridizes with a nucleic acid having a sequence of SEQ ID NO: 1, SEQ ID NO: 4 or SEQ ID NO: 7 or the complementary sequence to SEQ ID NO: 1, SEQ ID NO: 4 or SEQ ID NO: 7, under stringent conditions; or (d) a nucleic acid has at least about 85% sequence identity with the coding region of SEQ ID NO: 1, SEQ ID NO: 4 or SEQ ID NO: 7.

In a second embodiment, the invention provides cells with the nucleic acid of the invention, which preferably express the channel at the cell surface. In another embodiment, the invention provides a process for producing a GABA-gated chloride protein in a cell of the invention, preferably by: growing the cell in a medium; and inducing the expression of the GABA-gated chloride channel by adding an expression inducing agent into the medium. The invention further provides the GABA-gated chloride channel, for instance as isolated from a cell of the invention.

In another embodiment, the invention provides a method for characterizing a bioactive agent, the method comprising (a) providing a first assay composition comprising (i) a cell expressing a GABA-gated chloride channel or (ii) an isolated GABA-gated chloride channel comprising the amino acid sequence encoded by the nucleic acid of the vector, or the amino acid sequence resulting from cellular processing of the amino acid sequence encoded by the nucleic acid of the vector, (b) contacting the first assay composition with the bioactive ag[]ent or a prospective bioactive agent, and (c) measuring the binding of the bioactive agent or prospective bioactive agent or a cellular response mediated by a isolated GABA-gated chloride channel.

The invention further provides hybridization probes that selectively hybridize with a nucleic acid of the invention, or the complementary sequence thereof. The hybridization probe can be an amplification primer and the amplification conditions can be made sufficiently specific to amplify a GABA-gated chloride channel sequence from lepidoptera but not to amplify a GABA-gated chloride channel sequence from other insects such as Drosophila, Aedes, locust or beetle.

BRIEF DESCRIPTION OF THE DRAWINGS

FIG. 1 shows the sequences (nucleic acid [SEQ ID NO: 1] and protein [SEQ ID NO: 2]) of TBW-a2.

FIG. 2 shows the sequences (nucleic acid [SEQ ID NO: 4] and protein [SEQ ID NO: 5]) of TBW-a3.

FIG. 3 shows the sequences (nucleic acid [SEQ ID NO: 7] and protein [SEQ ID NO: 8]) of TBW-a1.

DEFINITIONS

For the purposes of this application, the following terms shall have the respective meanings set forth below.

Amplimer

An amplimer is a nucleic acid which is an amplified copy of a sequence of another nucleic acid. Amplimers are typically produced by an amplification process such as the polymerase chain reaction.

Bioactive agent

A bioactive agent is a substance such as a chemical that can act on a cell, virus, tissue, organ or organism to create a change in the functioning of the cell, virus, organ or organism. Preferably, the organism is an insect. In a preferred embodiment of the invention, the method of identifying bioactive agents of the invention is applied to organic molecules having molecular weight of about 1,000 or less.

Extrinsically-derived nucleic acid

Extrinsically-derived nucleic acids are nucleic acids found in a cell that were introduced into the cell, a parent or ancestor of the cell, or a transgenic animal from which the cell is derived through a recombinant technology.

Promoter functionally associated with a nucleic acid

An extrinsic promoter for a protein-encoding nucleic acid is a promoter distinct from that used in nature to express a nucleic acid for that protein. A promoter is functionally associated with the nucleic acid if in a cell that is compatible with the promoter the promoter can act to allow the transcription of the nucleic acid.

Prospective agent

Prospective agents are substances which are being tested by the screening method of the invention to determine if they affect the function of a GABA-gated chloride channel.

Sequence identity

"Identity," as known in the art, is a relationship between two or more polypeptide sequences or two or more polynucleotide sequences, as determined by comparing the sequences, particularly, as determined by the match between strings of such sequences. "Identity" is readily calculated by known methods (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). While there exist a number of methods to measure identity between two sequences, the term is well known to skilled artisans (see, for example, *Sequence Analysis in Molecular Biology; Sequence Analysis Primer;* and Carillo, H., and Lipman, D., SIAM *J. Applied Math.*, 48: 1073 (1988)). Methods commonly employed to determine identity between sequences include, but are not limited to those disclosed in Carillo, H., and Lipman, D., SIAM *J. Applied Math.*, 48:1073 (1988) or Needleman and Wunsch, *J. Mol. Biol.*, 48: 443–445, 1970, or the Lipman-Pearson FASTA algorithm (*Proc. Natl. Acad. Sci. USA* 85: 2444–2448, 1988). Computer programs for determining identity are publicly available. A preferred computer program for determining sequence identity is the program in Geneworks v 2.5 (Intelligenetics Inc, Mountain View, Calif.), which uses a progressive alignment procedure similar to FASTA. Preferably the parameters used with the Geneworks program are: cost to open gap=50, lengthen gap=100, minimum diagonal length=4, maximum diagonal offset=125. Other computer program methods to determine identity between two sequences include, but are not limited to, GCG program package (Devereux, J., et al., *Nucleic Acids Research* 12(1): 387 (1984)), BLASTP, BLASTN, and FASTA (Atschul, S. F. et al., *J. Molec. Biol.* 215: 403–410 (1990)). The BLAST X program is publicly available from NCBI (blast@ncbi.nlm.nih.gov)and other sources (*BLAST Manual,* Altschul, S., el al., NCBI NLM NIH Bethesda, Md. 20894; Altschul, S., et al., *J. Mol. Biol.* 215: 403–410 (1990)).

DETAILED DESCRIPTION OF THE INVENTION

The present invention relates to a number of nucleic acid and protein sequences. For the gene TBW-a2: SEQ ID NO:1 is a cDNA sequence encompassing the open reading frame; SEQ ID NO: 2 is the protein encoded by SEQ ID NO:1; and SEQ ID NO:3 is the same protein minus the signal peptide. For the gene TBW-a3: SEQ ID NO:4 is a cDNA; SEQ ID NO:5 is the protein sequence encoded by SEQ ID NO:4; and SEQ ID NO:6 is the same protein minus the signal peptide. For the gene TBW-a1: SEQ ID NO:7 is a cDNA sequence; and SEQ ID NO:8 is the protein sequence encoded by SEQ ID NO:9. The TBW-a2, TBW-a3 and TBW-a1 protein sequences are related to other insect GABA-gated chloride channels as set forth in the table below, where the relatedness values were determined using Geneworks v 2.5 program with the following parameters: cost to open gap=50, lengthen gap=100, minimum diagonal length=4, maximum diagonal offset=125.

| Sequence: | Percentage Identity | | | |
| --- | --- | --- | --- | --- |
| | Drosophila b[3] | TBW-a2 (SEQ ID NO:2) | TBW-a3 (SEQ ID NO:5) | Drosophila rdl[1] |
| Aedes rdl[2] | 28 | 72 | 74 | 75 |
| Drosophila b | | 32 | 31 | 28 |
| TBW-a2 (SEQ ID NO:2) | | | 84 | 64 |
| TBW-a3 (SEQ ID NO:5) | | | | 66 |

[1]Genebank Accession No. M69057, ffrench et al., Proc. Natl. Acad. Sci. USA 88: 7209–7213, 1991.
[2]Genebank Accession No. U28803, Thompson et al., FEBS Letters 325: 187–190, 1993.
[3]Genebank Accession No. L17436, Henderson et al., Biochem. Biophys. Res. Commun. 193: 474–482, 1993.

In FIG. 1, the apparent signal peptide is denoted with the three-letter amino acid code, while the remaining amino acid sequence is denoted with the one-letter code. The signal peptide was identified by an examination of the charge and polarity characteristics of the N-terminal portion, which examination shows the three domains (the n-region, h-region and c-region) typically associated with a signal peptide (Heijne and Abrahmsen, *FEBS Letters* 244: 439–446, 1989). Although the Ala Gly Ala sequence (amino acids 30–32) just preceding a run of four glycines is in compliance with the (−3, −1)-rule for identifying a signal peptide cleavage site, a weighted matrix analysis did not strongly identify a specific signal peptide cleavage site (Heijne, *J. Membr. Biol.* 115: 195–201, 1986). In FIG. 2, the apparent signal peptide of TBW-a3 is shown. The present invention further relates to isolated proteins in which these signal proteins are removed or substituted with another signal sequence. The substitution of one signal sequence with another and expression of the resulting proteins is illustrated, for the echistatin protein expressed in Sf9 cells, by Daugherty et al., *DNA Cell Biol.* 9: 453–9, 1990. These authors also describe the use of computer-aided signal peptide selection.

Further, in FIG. 1, the dashed underlining in the region encoding TBW-a2 indicates a "beta cysteine loop" that is characteristic of the ligand gated channel superfamily. The underlined four peptide sequences are apparent transmembrane segments. Also underlined is an AATAAA consensus polyadenylation/cleavage signal. In FIG. 2, the first underlining in the region encoding TBW-a3 indicates the beta cysteine loop. The next four underlined peptide sequences are apparent transmembrane segments.

By analogy to other GABA-gated chloride channels, it is likely that the functional protein is multimeric. See, e.g., Sieghart, *Pharmacol. Reviews* 47: 191–234, 1995. Insect channels are believed to typically be homooligomers.

Nucleic Acid—Encoding GABA-gated Chloride Channel

To construct non-naturally occurring GABA-gated chloride channel-encoding nucleic acids, the native sequences can be used as a starting point and modified to suit particular needs. For instance, the sequences can be mutated to incorporate useful restriction sites. See Maniatis et al. *Molecular Cloning, a Laboratory Manual* (Cold Spring Harbor Press, 1989). Such restriction sites can be used to create "cassettes", or regions of nucleic acid sequence that are facilely substituted using restriction enzymes and ligation reactions. The cassettes can be used to substitute synthetic sequences encoding mutated GABA-gated chloride channel amino acid sequences. Alternatively, the GABA-gated chloride channel-encoding sequence can be substantially or fully synthetic. See, for example, Goeddel et al., *Proc. Natl. Acad. Sci. USA,* 76: 106–110, 1979. For recombinant expression purposes, codon usage preferences for the organism in which such a nucleic acid is to be expressed are advantageously considered in designing a synthetic GABA-gated chloride channel-encoding nucleic acid. For example, a nucleic acid sequence incorporating prokaryotic codon preferences can be designed from a eukaryotic-derived sequence using a software program such as Oligo-4, available from National Biosciences, Inc. (Plymouth, Minn.).

The nucleic acid sequence embodiments of the invention are preferably deoxyribonucleic acid sequences, preferably double-stranded deoxyribonucleic acid sequences. However, they can also be ribonucleic acid sequences, or nucleic acid mimics, meaning compounds designed to preserve the hydrogen bonding and base-pairing properties of nucleic acid, but which differ from natural nucleic acid in, for example, susceptibility to nucleases.

Numerous methods are known to delete sequence from or mutate nucleic acid sequences that encode a protein and to confirm the function of the proteins encoded by these deleted or mutated sequences. Accordingly, the invention also relates to a mutated or deleted version of a nucleic acid sequence that encodes a protein that retains the ability to transport chloride across a membrane, especially if such transport is turned on or enhanced by the presence of GABA. These analogs can have N-terminal, C-terminal or internal deletions or substitutions, so long as GABA-gated chloride channel function is retained. The point variations are preferably conservative point variations. Preferably, the analogs will have at least about 85% sequence identity, preferably at least about 90%, more preferably at least about 95% still more preferably at least about 98% yet still more preferably at least about 99.5%, to the corresponding protein sequence of SEQ ID NO: 3, SEQ ID NO: 6 or SEQ ID NO: 8.

Mutational and deletional approaches can be applied to all of the nucleic acid sequences of the invention that express GABA-gated chloride channel proteins. As discussed above, conservative mutations are preferred. Such conservative mutations include mutations that switch one amino acid for another within one of the following groups:

1. Small aliphatic, nonpolar or slightly polar residues: Ala, Ser, Thr, Pro and Gly;
2. Polar, negatively charged residues and their amides: Asp, Asn, Glu and Gln;
3. Polar, positively charged residues: His, Arg and Lys;
4. Large aliphatic, nonpolar residues: Met, Leu, Ile, Val and Cys; and
5. Aromatic residues: Phe, Tyr and Trp.

A preferred listing of conservative variations is the following

| Original Residue | Variation |
| --- | --- |
| Ala | Gly, Ser |
| Arg | Lys |
| Asn | Gln, His |
| Asp | Glu |
| Cys | Ser |
| Gln | Asn |
| Glu | Asp |
| Gly | Ala, Pro |
| His | Asn, Gln |
| Ile | Leu, Val |
| Leu | Ile, Val |
| Lys | Arg, Gln, Glu |
| Met | Leu, Tyr, Ile |
| Phe | Met, Leu, Tyr |
| Ser | Thr |
| Thr | Ser |
| Trp | Try |
| Tyr | Trp, Phe |
| Val | Ile, Leu |

The types of variations selected may be based on the analysis of the frequencies of amino acid variations between homologous proteins of different species developed by Schulz et al., *Principles of Protein Structure,* Springer-Verlag, 1978, on the analyses of structure-forming potentials developed by Chou and Fasman, *Biochemistry* 13: 211, 1974 and *Adv. Enzymol.,* 47: 45–149, 1978, and on the analysis of hydrophobicity patterns in proteins developed by Eisenberg et al., *Proc. Natl. Acad. Sci. USA* 81: 140–144, 1984; Kyte & Doolittle; *J. Molec. Biol.* 157: 105–132, 1981, and Goldman et al., *Ann. Rev. Biophys. Chem.* 15: 321–353, 1986. All of the references of this paragraph are incorporated herein in their entirety by reference.

For the purposes of this application, a nucleic acid of the invention is "isolated" if it has been separated from other macromolecules of the cell or tissue from which it is derived.

Nucleic Acid Probes

It will be recognized that many deletional or mutational analogs of nucleic acid sequences for a GABA-gated chloride channel will be effective hybridization probes for GABA-gated chloride channel-encoding nucleic acid. Accordingly, the invention relates to nucleic acid sequences that hybridize with such GABA-gated chloride channel-encoding nucleic acid sequences under selection conditions. Preferably, the nucleic acid sequence selects for the nucleic acid sequence encoding SEQ ID NO: 3, SEQ ID NO: 6 or SEQ ID NO: 8. Probing can comprise, for example, hybridization, Rnase protection or amplification.

"Selective conditions" refers to conditions that allow for the identification of substantially related nucleic acid sequences; and, in this context, refers to conditions that distinguish GABA-gated chloride channel from the reported Drosophila, beetle and roach rdl or rdl-related genes. For instance, for hybridization such conditions are stringent conditions that will generally allow hybridization of sequence with at least about 85% sequence identity, preferably with at least about 90% sequence identity, more preferably with at least about 95% sequence identity, for example with a nucleic acid encoding SEQ ID NO: 3, SEQ ID NO: 6 or SEQ ID NO: 8. Such hybridization conditions are described by Sambrook et al., *Molecular Cloning: A Laboratory Manual,* 2nd ed., Cold Spring Harbor Press, 1989. For example, such conditions include overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml denatured, sheared salmon sperm DNA, followed by washing the filters in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein, the disclosure of which is hereby incorporated in its entirety by reference. Hybridization conditions and probes can be adjusted in well-characterized ways to achieve selective hybridization of probes.

Nucleic acid molecules that will hybridize to a GABA-gated chloride channel-encoding nucleic acid under stringent conditions can be identified functionally, using methods outlined above, or by using for example the hybridization rules reviewed in Sambrook et al., *Molecular cloning: A Laboratory Manual,* 2nd ed., Cold Spring Harbor Press, 1989.

Without limitation, examples of the uses for nucleic acid probes include: histochemical uses such as identifying tissues that express the GABA-gated chloride channel; measuring mRNA levels, for instance to identify a sample's tissue type or to identify cells that express abnormal levels of GABA-gated chloride channel; and detecting polymorphisms in the GABA-gated chloride channel gene. RNA hybridization procedures are described in Maniatis et al. *Molecular Cloning, a Laboratory Manual* (Cold Spring Harbor Press, 1989).

Amplification Primers

Rules for designing polymerase chain reaction ("PCR") primers are now established, as reviewed by *PCR Protocols,* Cold Spring Harbor Press, 1991. Degenerate primers, i.e., preparations of primers that are heterogeneous at given sequence locations, can be designed to amplify nucleic acid sequences that are highly homologous to, but not identical to, a GABA receptor-encoding nucleic acid. Strategies are now available that allow for only one of the primers to be required to specifically hybridize with a known sequence. See, Froman et al., *Proc. Natl. Acad. Sci. USA* 85: 8998, 1988 and Loh et al. *Science* 243: 217, 1989. For example, appropriate nucleic acid primers can be ligated to the nucleic acid sought to be amplified to provide the hybridization partner for one of the primers. In this way, only one of the primers need be based on the sequence of the nucleic acid sought to be amplified.

PCR methods of amplifying nucleic acid will utilize at least two primers. One of these primers will be capable of hybridizing to a first strand of the nucleic acid to be amplified and of priming nucleic acid synthesis in a first direction. The other will be capable of hybridizing the reciprocal sequence of the first strand (if the sequence to be amplified is single stranded, this sequence will initially be hypothetical, but will be synthesized in the first amplification cycle) and of priming nucleic acid synthesis from that strand in the direction opposite the first direction and towards the site of hybridization for the first primer. Conditions for conducting such amplifications, particularly under preferred stringent hybridization conditions, are well known. See, for example, *PCR Protocols,* Cold Spring Harbor Press, 1991.

Other amplification procedures are available that utilize oligonucleotides to direct the specificity of the amplification, such as the ligase chain reaction (LCR). LCR uses the source nucleic acid as a template to bring two probe oligonucleotides close to one another to allow ligation (with or without provision for polymerization to fill in relatively small gaps between the probes). Upon ligation, the two linked probes provide additional template for the next cycle of the reaction. As with PCR, approaches can be devised to use a single probe corresponding to the source nucleic acid. The present invention also encompasses oligonucleotides designed to specifically identify GABA-gated chloride channels.

Vectors

A suitable expression vector is capable of fostering expression of the included GABA-gated chloride channel encoding DNA in a host cell, which can be eukaryotic, fungal, or prokaryotic. Suitable expression vectors include pRc/CMV (Invitrogen, San Diego, Calif.), pRc/RSV (Invitrogen), pcDNA3 (Invitrogen), Zap Express Vector (Stratagene Cloning Systems, La Jolla, Calif.); pBk/CMV or pBk-RSV vectors (Stratagene), Bluescript II SK +/− Phagemid Vectors (Stratagene), LacSwitch (Stratagene), pMAM and pMAM neo (Clontech, Palo Alto, Calif.), pKSV10 (Pharmacia, Piscataway, N.J.), pCRscript (Stratagene) and pCR2.1 (Invitrogen), among others. Useful yeast expression systems include, for example, pYEUra3 (Clontech). Useful baculovirus vectors include several viral vectors from Invitrogen (San Diego, Calif.) such as pVL1393, pVL1392, pBluBac2, pBluBacHis A, B or C, and pbacPAC6 (from Clontech). A preferred vector is any of the pIE1-series vectors (Novagen, Madison Wis.) utilizing the EIP (early inducible promoter) baculovirus promoters for expression in Sf9 or Sf21 cells. Of course, expression can simply comprise expression of in vitro produced RNA in a cell or a cell-free system. In some embodiments, inducible promoters are preferred.

Cells

In one embodiment of the invention, the channel is expressed in a eukaryotic cell line, preferably a transformed cell line with an established cell culture history. In this embodiment, particularly preferred cell lines include lepidopteran cells such as Sf9 and Sf21 cells (available for example from Clontech, Palo Alto, Calif.) and Drosophila cells such as Schneider-2 or Kc cells. Other useful cells include mammalian cells such as COS or CHO cells, fungal cells such as yeast cells, and bacterial cells. Considerations for expressing membrane-bound receptors in bacteria can be found in Freissmuth et al., "Expression of two human beta-adrenergic receptors in *Escherichia coli,*" *Proc. Natl. Acad. Sci. USA* 88: 8548–8552, 1991 and Herzog et al., "Human neuropeptide Y1 receptor expressed in Escherichia coli retains its pharmacological properties," *DNA Cell Biol.* 13: 1221–1225, 1994.

Isolated GABA-gated Chloride Channel

The invention also provides for the GABA-gated chloride channel proteins encoded by any of the nucleic acids of the invention preferably in a purity achieved, for example, by applying protein purification methods, such as those described below, to a lysate of a recombinant cell according to the invention.

The GABA-gated chloride channel variants of the above paragraphs can be used to create organisms or cells that produce GABA-gated chloride channel activity. Purification methods, including associated molecular biology methods, are described below.

Method of Producing GABA-gated Chloride Channel

One simplified method of isolating polypeptides synthesized by an organism under the direction of one of the nucleic acids of the invention is to recombinantly express a fusion protein wherein the fusion partner is facilely affinity purified. For instance, the fusion partner can be glutathione S-transferase, which is encoded on commercial expression vectors (e.g., vector pGEX4T3, available from Pharmacia, Piscataway, N.J.). The fusion protein can then be purified on a glutathione affinity column (for instance, that available from Pharmacia, Piscataway, N.J.). Of course, the recombinant polypeptides can be affinity purified without such a fusion partner using an appropriate antibody that binds to GABA-gated chloride channel. Methods of producing such antibodies are available to those of ordinary skill in light of the ample description herein of GABA-gated chloride channel expression systems and known antibody production methods. See, for example, Ausubel et al., *Short Protocols in Molecular Biology,* John Wiley & Sons, New York, 1992.

If fusion proteins are used, the fusion partner can be removed by partial proteolytic digestion approaches that preferentially attack unstructured regions such as the linkers between the fusion partner and GABA-gated chloride channel. The linkers can be designed to lack structure, for instance using the rules for secondary structure forming potential developed, for instance, by Chou and Fasman, *Biochemistry* 13: 211, 1974 and Chou and Fasman, *Adv. in Enzymol.* 47: 45–147, 1978. The linker can also be designed to incorporate protease target amino acids, such as, arginine and lysine residues, the amino acids that define the sites cleaved by trypsin. To create the linkers, standard synthetic approaches for making oligonucleotides can be employed together with standard subcloning methodologies. Other fusion partners besides GST can be used. Procedures that utilize eukaryotic cells, particularly mammalian cells, are preferred since these cells will post-translationally modify the protein to create molecules highly similar to or functionally identical to native proteins.

Additional purification techniques can be applied, including without limitation, preparative electrophoresis, FPLC (Pharmacia, Uppsala, Sweden), HPLC (e.g., using gel filtration, reverse-phase or mildly hydrophobic columns), gel filtration, differential precipitation (for instance, "salting out" precipitations), ion-exchange chromatography and affinity chromatography.

Because GABA-gated chloride channel is a membrane protein, which by analogy to related channel proteins is believed to have four transmembrane sequences, isolation methods will often utilize detergent extractions, generally using detergents such as non-ionic detergents selected to maintain the appropriate secondary and tertiary structure of the protein. See, for example, Hjelmeland, "Solubilization of native membrane proteins," in *Methods in Enzymol.,* Vol. 182, M. P. Deutscher, ed., Academic Press, San Diego, Calif., pp. 253–264, 1990 and Thomas and McNamee, "Purification of membrane proteins," in *Methods in Enzymol.,* Vol. 182, pp. 499–520, 1990. For a description of methods for re-integrating a solubilized channel into a membrane, see Ohta et al., "Dynamic structures of adrenocortical cytochrome P-450 in proteoliposomes and microsomes: protein rotation study," *Biochemistry* 31: 12680–7, 1992 and Krishnaswamy et al., "Role of the membrane surface in the activation of human coagulation factor X," *J. Biol. Chem.* 267: 26110–20, 1992. Integral proteins typically have at least one domain that extends away from the cell surface or other membrane.

The isolation of GABA-gated chloride channel can comprise isolating membranes from cells that have been transformed to express GABA-gated chloride channel. Preferably, such cells express GABA-gated chloride channel in sufficient copy number such that the amount of GABA-gated chloride channel in a membrane fraction is at least about 10-fold higher than that found in comparable membranes from cells that naturally express GABA-gated chloride channel, more preferably the amount is at least about 100-fold, or still more preferably at least about 1000-fold, higher. If needed, specific membrane fractions, such as a plasma membrane fraction, can be isolated.

For the purposes of this application, GABA-gated chloride channel is "isolated" if it has been separated from other proteins or other macromolecules of the cell or tissue from which it is derived. Preferably, the composition containing GABA-gated chloride channel is at least about 10-fold enriched, preferably at least about 100-fold, with respect to protein content, over the composition of the source cells.

Method of Characterizing or Identifying Agent

A method for the analysis of or screening for a bioactive agent, for instance for use as an insecticide, comprises determining some measure of activity of a bioactive agent or a prospective bioactive agent mediated by a recombinant GABA-gated chloride channel. This determining can include culturing multiple (two or more) cell cultures, wherein the cultures are preferably of the same species, more preferably of the same strain or cellular subtype thereof and the cells of each culture includes an nucleic acid encoding a recombinant GABA-gated chloride channel as described herein. At least some of the cultures are contacted with bioactive agent or prospective bioactive agent, while controls are treated in parallel except that they are not contacted with bioactive agent or prospective bioactive agent. Binding activities can be identified, or other cellular responses, such as chloride conductance, can be monitored to provide an indication of whether a bioactive agent or prospective bioactive agent acts on the cells and is an agonist or antagonist. Preferably, cells are contacted with a bioactive agent or prospective agent that is an organic compound. Binding of a bioactive agent or prospective bioactive agent can be determined directly, in which case the prospective agent usually incorporates a radioisotope, such as $^3$H or $^{14}$C, or through competition with a labeled, known ligand. The results are then compared to results with cells that were not contacted with the bioactive agent or prospective bioactive agent (i.e., the control cell). Alternatively, particularly for binding assays, an assay can utilize a composition comprising an isolated GABA-gated chloride channel in place of cells.

A ligand used in a binding assay is preferably radiolabeled with any detectable isotope, such as radioactive isotopes of iodide, carbon or hydrogen. Specific binding of the radiolabeled ligand is then determined by subtracting the radioactivity due to non-specific binding from that which is due to total (i.e., specific and non-specific) binding of the radiolabeled ligand. The radioactivity due to non-specific binding is determined by measuring, the amount of radiolabel associated with a GABA-gated chloride channel that has been contacted with both radiolabeled ligand and a significant excess of non-radiolabeled ligand, such as a 1,000-fold excess. The radioactivity due to total binding of the radiolabeled ligand is determined by measuring the amount of radiolabel bound to the receptor preparation in the absence of non-radiolabeled ligand.

A bioactive agent that affects a GABA-gated chloride channel of the invention can have a contrasting activity profile with respect to another GABA-gated chloride channel. In one embodiment, a preferred bioactive agent has specific; y to bind GABA-gated chloride channel of the invention with at least about 50-fold greater affinity than its binding to one other GABA-gated chloride channel, more preferably at least about 500-fold greater affinity. The bioactive agent can be any compound, material, composition, mixture, or chemical, that can be presented to a receptor in a form that allows for the agent to diffuse so as to contact the receptor. Other suitable bioactive agents in the context of the present invention include small organic compounds, preferably of molecular weight between about 100 daltons and about 1,000 daltons, and are composed of such functionalities as alkyl, aryl, alkene, alkyne, halo, cyano and other groups, including heteroatoms or not. The chemicals tested as prospective agents can be prepared using combinatorial chemical processes known in the art or conventional means for chemical synthesis.

Additional indicators of cellular responses to a bioactive agent include, for example: flux of radioactive [$^{36}$Cl] chloride ions; chlorine sensitive fluorescent probes (e.g. SPQ (6-methoxy-N-(3-sulfopropyl)quinolinium)); or changes in intercellular membrane potential measured by electrophysiological methods such as the patch clamp or with redox sensitive dyes such as acridine orange.

The following examples further illustrate the present invention, but of course, should not be construed as in any way limiting its scope.

EXAMPLE 1

GABA-gated Chloride Channel Sequence Identifications

Materials and Methods

TBW polyA RNA isolation. DEPC was prepared to 0.1% in water, incubating at 37 C. overnight, then autoclaving for 60 minutes. All glassware was baked for 4 h at 250° C., bottle caps were soaked in 0.1% DEPC. The microprobe of a Braun homogenizer was soaked in 50 mls 100% EtOH, then run in 25 mls RNAzolB (a guanidinium hydrochloride preparation from CINNA-BIOTECX Labs, Inc., Houston, Tex.). Fourth instar TBW larvae were frozen in weigh boats placed on dry ice, heads were excised with razor blades and sets of 100 heads were collected in round bottom centrifuge tubes. The excised heads were homogenized at full speed for 30 s at room temperature. Extraction buffer (3 ml) from a Pharmacia Biotech QuickPrep Micro mRNA Purification kit (Pharmacia Biotech Inc., Piscataway, N.J.) was added and homogenization was continued for 10 s. The macerate was clarified by centrifugation at 12,000 g in an SS34 rotor for 10 minutes at RT. The supernatant was batch processed on oligo-dT spin columns from PMK as specified by the manufacturer. Three elutions totaling 1.5 ml were pooled and the RNA quantified by UV spectrometry.

Synthesis of first strand cDNA. Reverse transcription was initiated by addition of cloned Maloney Murine Leukemia Virus (M-MLV) reverse transcriptase to 0.5 μg template RNA in the presence of all four dNTPs. The reactions were placed on a Geneamp 9600 (Perkin-Elmer-ABI, Foster City, Calif.) thermal cycler and held at 42° C. for 30 min; the M-MLV RT was then inactivated by heating to 99° C. for 5 min followed by 5 min at 5° C.

PCR amplification. The 20 μl cDNA reaction was made to 100 μl utilizing buffers and dNTPs supplied in a Perkin Elmer, Amplitaq based RT-PCR kit according to the manufacturers protocol. Amplifications utilizing degenerate primers typically employed annealing temperatures of 45–48° C., those involving isoform specific primers used annealing temperatures in the range of 55 to 60° C. RACE reactions were carried out using primers and protocols supplied with the GIBCO BRL 5' and 3' RACE kits (GIBCO-BRL, Bethesda, Md.). The PCR products were characterized by agarose gel electrophoresis. When secondary "nested" amplifications were carried out, bands were excised from NuSieve gels (FMC Corp.,) and remelted by heating to 70° C. The molten agarose was diluted 1:1 with warm water and a 1:5 μl aliquot was transferred directly to a second 100 μl amplification.

Genomic DNA Isolations. Genomic DNA was isolated and purified from 10 to 20 TBW larvae with reagents and protocols provided in a Pharmacia Biotech RapidPrep Macro Genomic DNA kit (Pharmacia, Piscataway, N.J.), genomic isolations from individual larvae were made with the micro version of the same system. Amplifications using anchor adaptor ligated genomic DNA as template followed the strategy outlined by Roux et al. (*Bio Techniques* 8: 48–57, 1990).

Primer synthesis and design. Oligonucleotides were synthesized on an ABI model 392 DNA synthesizer (Perkin-Elmer-ABI, Foster City, Calif.) using reagents and procedures supplied by the manufacturer. The reaction products were isolated on ABI/PE OPC columns (Perkin-Elmer-ABI, Foster City, Calif.) and used without further purification. Biotinylated sequencing primers were made using the fifth bottle position on the synthesizer. PCR primers and probes were designed and annealing temperatures estimated using the OLIGO 4.0 program from NBI Scientific Software (Plymouth, Minn.).

Subcloning and sequencing. Proteins were removed from PCR reactions by three extractions with Strataclean resin as specified by Stratagene Corp. (La Jolla, Calif.). If the primers included engineered restriction sites, they were then digested. More routinely, the amplimers were blunt ended by filling with Klenow polymerase treatment, then phosphorylated by routine procedures (Sambrook et al., 1989). The amplimers were then gel purified on Seaplaque or NuSieve gels (FMC Corp) and extracted from the agarose using a QIAEX kit (QIAGEN Corp., Chatsworth, Calif.). Alkaline lysis plasmid isolations and purifications were carried out with a Qiatip kit following the recommendations of QIAGEN Corp. Thermal cycle sequencing reactions utilized 5'-end labeled biotinylated sequencing primers and a Promega fmol sequencing kit (Promega, Madison, Wis.). Reactions products were separated on 6% Long Ranger (FMC Corp) 7M Urea manual gels, then the biotinylated ladders were transferred to Immobilon (Millipore Corp., Bedford, Mass.) membranes and developed with a Phototope chemiluminesent kit following protocols developed by New England Biolabs (Beverly, Mass.). Alternatively, dye terminator cycling reactions were carried out with a Perkin Elmer Amplitaq FS sequencing kit and the reaction products were analyzed on 5% Long Ranger gels run in an ABI Prizm 377 automated DNA sequencer (Perkin-Elmer-ABI, Foster City, Calif.). Five to 10 clones carrying a PCR reaction product were sequenced in both directions until a consensus could be achieved between multiple clones as a means of avoiding errors in nucleotide assignments due to thermal polymerase mis-incorporations. Sequencing contigs were assembled using the Intelligenetics GeneWorks program (Intelligenetics, Mountain View, Calif.).

Primers. The primers utilized were as follows:

TBW-a2 sequence was extended downstream by reverse transcribing mRNA with AP. The cDNA was then amplified by PCR reactions between Primer 13 and AP followed by a nested reaction between Primer 16 and the Universal Anchor Primer ("UAP") provided in the GIBCO-BRL 3'-RACE

| Primer | Sequence | Translation | Orientation |
|---|---|---|---|
| 1 (#9)* | GCRAANACCATNACRAARCA | | reverse |
| 5 (#10) | GTNGTCATNGTSAGNACNGT | | reverse |
| 6 (#11) | TGGGTNCCNGAYACNIT | WVPDTF | forward |
| 7 (#12) | CC<u>GAGCTC</u>SWRTAYTTRTCDATRTC | | reverse |
| 8 (#13) | CC<u>GAGCTC</u>ARRTADATDATCCARTACAT | | reverse |
| 9 (#14) | AG<u>GCGGCCGC</u>GGNGTNACNATGTAYGT | GVTMYV | forward |
| 10 (#15) | CT<u>GCGGCCGC</u>CARTTYTGGACNGAYCC | QFWIDP | forward |
| 11 (#16) | AA<u>TCTAGA</u>GGGTGTCTTTCTGGTTG | VSFWL | forward |
| 12 (#17) | AG<u>CTCGAG</u>AGTTTCGGCTACACCAT | SFGYTM | forward |
| 13 (#18) | TT<u>CTCGAG</u>CGATGGATTTGCACTATTTTC | MDLQYF | forward |
| 14 (#19) | CAGAGCTCATTTCACATGCCAGACGAGAG | | reverse |
| 15 (#20) | TA<u>GAGCTC</u>GAATGATGAATGCGTATGAAT | FIRIHH | forward |
| 16 (#21) | TC<u>TCTAGA</u>TACGCTCGATGGGATAC | RSMGY | forward |
| 24 (#22) | TT<u>GCGGCCGC</u>CATATATCCCACAG | | reverse |
| 25 (#23) | CT<u>GCGGCCGC</u>TCGAGCTGGTG | | reverse |
| 26 (#24) | CGGATGAATTCATTGCTGGTTGTT | | reverse |
| 27 (#25) | CTGTCGATCCATCGGGAAGTATTG | | reverse |
| 31 (#26) | GCGGACCTCCATAGTTTGGTC | | reverse |
| 34 (#27) | CAGACGAAGAAGCTGGACCACCTC | DEEAGPPP | forward |
| 35 (#28) | ACGCGGCCGCAAGGACATAAGCAA | KDISK | forward |

*The SEQ ID numbers are in parentheses.

The degenerate primers among the above oligonucleotides incorporate a statistical mix of monomers at the positions labeled N (A, G, C or T), H (A, C or T), S (C or G), Y (C or T), W (A or T), D (A, G or T) or R (A or G) [in accordance with IUPAC convention]. The underlined sequences are restriction sites.

TBW-a1 Sequence Amplifications

All amplification descriptions for TBW-a1 designate sequence positions with respect to the corresponding sequences of TBW-a2 set forth in FIG. 1.

In a nested PCR reaction, first Primers 6 and 1, and then Primers 6 and 5 were used to amplify a fragment from nucleotides 493 to 970 (excluding 37 bases from the primers) of TBW-a1, which was cloned and sequenced. It will be recognized, for this amplification and in the other amplifications from mRNA described herein, that the amplification substrate was produced by reverse transcription with a reverse primer, in this case with Primer 1. This sequence included the unique PARVQL motif discussed above. This sequence is not a result of polymerase misincorporation of sequencing error since it was found in clones arising from separate mRNA preparations, clones were sequenced on both strands, and restriction analyses of a number of clones confirmed the presence of a PvuII site that is dependent on the Gln codon.

TBW-a1 sequence was extended downstream by reverse transcribing mRNA with the poly T Adapter Primer ("AP") provided in the GIBCO-BRL 3'-RACE system. The cDNA was then amplified by PCR reactions between Primer 12 and AP followed by a nested reaction between Primer 11 and AP generating an amplimer from 929–1157. The amplimer was isolated, cloned, and sequenced.

TBW-a2 Sequence Amplifications

TBW mRNA was reverse transcribed with Primer 1, then PCR reactions were conducted first between Primers 6 and 1 followed by a nested reaction between Primers 6 and 5 yielding a fragment from 493 to 970 of TBW-a2. The amplified fragment was cloned and sequenced. This fragment included the PARVSL motif discussed above.

system; generating an amplimer from 862–1154. The amplimer was isolated, cloned, and sequenced.

TBW-a2 sequence was extended further downstream by reverse transcribing mRNA with Primer 8. The cDNA was then amplified by PCR reactions between Primer 11 and 8 followed by a nested reaction between Primer 11 and 7, generating an amplimer from 929 to 1462 of TBW-a2, which was cloned and sequenced.

The translational stop signal of the TBW-a2 sequence was revealed by a reapplication of the 3' RACE strategy. TBW mRNA was reverse transcribed with the AP provided in the GIBCO-BRL 3'-RACE system. The cDNA was then amplified by PCR reactions between Primer 16 and AP followed by a nested reaction between Primer 34 and AP generating an amplimer from 1407–1824 including 230 bp of 3' untranslated region (UTR).

The translational start signal of the TBW-a2 sequence was revealed by a 5' RACE strategy. TBW mRNA was reverse transcribed with Primer 14, the resulting single stranded cDNA had a homopolymeric dCn tail added to the 3' end using Terminal deoxynucleotidyl Transferase (TdT) as outlined in the GIBCO BRL 5' RACE kit version 2.0. The cDNA was then amplified by PCR reactions between Primer 15 and the Abridged Anchor Primer (AAP) followed by a nested reaction between Primer 15 and UAP; generating an amplimer from 1–543 including 103 bp of 5' untranslated region.

TBW-a3 Sequence Amplifications

Initial TBW-a3 sequence was isolated by reverse transcribing mRNA with Primer 8. The cDNA was then amplified by PCR reactions between Primer 11 and 8 followed by a nested reaction between Primer 11 and 7; generating an amplimer from 805–1314.

The TBW-a3 sequence was extended further upstream by reverse transcribing mRNA with Primer 24. The cDNA was then amplified by PCR reactions between Primer 9 and 24 followed by a nested reaction between Primer 10 and 25; generating an amplimer from 282–817.

The TBW-a3 sequence was extended upstream into the signal peptide by a 5' RACE strategy. TBW mRNA was reverse transcribed with Primer 29, the resulting single stranded cDNA had a homopolymeric $dC_n$ tail added to the 3' end using Terminal deoxynucleotidyl Transferase (TdT) as outlined in the GIBCO BRL 5' RACE kit version 2.0. The cDNA was then amplified by PCR reactions between Primer 27 and AP followed by a nested reaction between Primer 26 and UAP; generating an amplimer from 53–404. The process was then repeated, this time following the reverse transcription reaction with PCR reactions between Primer 26 and AAP followed by a nested reaction between Primer 31 and UAP; generating an amplimer from 1–154.

The translational stop signal of the TBW-a3 sequence was revealed by a reapplication of the 3' RACE strategy. TBW mRNA was reverse transcribed with the AP provided in the GIBCO-BRL 3'-RACE system. The cDNA was then amplified by PCR reactions between Primer 35 and AP followed by a nested reaction between Primer 35 and UAP generating an amplimer from 1293–1519 including 72 bp 3' untranslated region (UTR).

Amplifications of mRNA derived from individual TBW larvae, and confirmatory restriction length analyses, confirmed that both TBW-a2 and TBW-a3 are be found in the same individual.

EXAMPLE 2
Expression Vectors

Primers. The primers utilized were as follows:

| Primer | Sequence | Translation | Orientation |
|---|---|---|---|
| 13(#29) | TTCTCGAGCGATGGATTTGCACTATTTTC | MDLQYF | forward |
| 17(#30) | AGTCCCGGCGGCAGGCTGATA | 5'UTR | forward |
| 18(#31) | ATGACAATTAGGCCAGACGGAATA | | reverse |
| 19(#32) | CATCCGATACAAGTGGAATG | IRYKWNE | forward |
| 20(#33) | GTCGACCCAGTGCCAATATACACGAC | 3'UTR | reverse |
| 21(#34) | GTCGACTTACCGAAACTTGATGGATG | 3'UTR | reverse |
| 24(#35) | TTGCGGCCGCCATATATCCCACAG | | reverse |
| 28(#36) | GTGAAATACAATTCGTTCGGTCTA | EIQFVRS | forward |
| 30(#37) | GCAGATGTGGAAAATAAGTGGATT | 3'UTR | reverse |
| 32(#38) | AGCGAATACCATGACGAAACA | | reverse |
| 33(#39) | GCGGCCGCCTTCCTAC | AAAFLP | forward |
| 36(#40) | ACCATCCATTTAGACGACGC | 5'UTR | forward |
| 37(#41) | GTAACACCAACTTCCACCG | | reverse |
| 38(#42) | GAATGGCCAACATGTCGCTGGAAATC | MSLEI | forward |
| 39(#43) | AATAATGACGTCACCGAACATCCCTCCCC CACCG | | reverse |

TWA-a2

Two overlapping pieces of TBW-a2 were amplified, and a unique NcoI site was used to ligate the two pieces into a complete TBW-a2 sequence. The 3' piece was created by using Primer 18 to prime reverse transcription (beginning at base 879), followed by PCR with Primers 17 and 18. The 5' piece was created by using Primer 20 to prime reverse transcription (beginning at base 1764), followed by nested PCR with, first, Primers 13 and 20, then Primers 19 and 21. The amplimers were cut with NcoI, polished, phosphorylated and ligated into a blunt-ended cloning site of a first vector. The insert from the first vector is used to provide an insert for one or more expression vectors. Or a vector with a T7 or Sp6 promoter is used, and RNA created from the vector is expressed by injection into a cell such as Xenopus oocyte.

TBW-a3

For the a3 sequence the same strategy was followed in order to generate a vector that serves as a depository for the sequence. In order to add a translational start site, the first step was to construct a chimera by adding the Aedes aegypti signal peptide from its rdl gene to the 5' end of the TBW GABA a3. The Aedes signal peptide was prepared in a two-step approach whereby it was first isolated using primers that exactly matched its sequence, and then was modified using highly engineered primers. Mosquito larvae were grown in-house and extracted for mRNA in the same manner as had been done for the TBW larvae heads. The signal peptide sequence was then reverse transcribed with Primer 37 and the cDNA amplified by PCR between Primer 36 and Primer 37 yielding a fragment from bp 556–909 (using the numbering of GenBank accession M69057). The amplimer was polished, phosphorylated and ligated into SmaI cut pUC18 and fully sequenced and found to be in complete agreement with the GenBank deposit. This purified plasmid was then used as a template in a PCR reaction between Primer 38 and Primer 39 which amplified and modified the sequence from 670–842 (bp 696–808 lying between the primers) of the Aedes signal peptide; the bp 681–683 code for the ATG Met start signal. This reaction introduced an MscI site at the 5' end, and an AatII site at the 3' end and changed bp 815 to 842 from Aedes to TBW sequence. This engineered fragment was then ligated to an endogenous AatII site in the TBW-a3 signal peptide (between bp 101 and 102) by digesting a TBW-a3 5' piece (a Primer 28 and 30 amplimer, created by nested reaction after an initial amplification with Primers 33 and 24) with AatII. This chimeric fragment was then combined with the 3' piece (the Primer 32 and 33 amplimer) by use of the unique XhoI site.

The nucleic acid sequences described herein, and consequently the protein sequences derived therefrom, have been carefully sequenced. However, those of ordinary skill will recognize that nucleic acid sequencing technology can be susceptible to some error. Those of ordinary skill in the relevant arts are capable of validating or correcting these sequences based on the ample description herein of the nucleic acid sequences and of methods of isolating these nucleic acid sequences. Thus such corrected sequences, and such modifications that are made readily available by the present disclosure, are encompassed by the present invention. Furthermore, those sequences reported herein are within the invention whether or not later clarifying studies identify sequencing errors.

The Aedes signal peptide/Heliothis GABA a3 (Ala) chimera described above was assembled and cloned into the MscI/SalI sites of a Novagen pT7Blue-2 Xenopus transcription vector placing it under the control of a T7 promoter. This plasmid was stored and designated as pT7HGABA-a3. The Heliothis GABA a2 (Ser) isoform was assembled and cloned into the PmeI/BamHI sites of a Novagen pIE1-3 baculovirus expression vector placing it under the control of the ie1 baculovirus promoter. This plasmid was stored and designated as pIE3HGABA-a2.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed is:
1. An isolated polypeptide comprising SEQ ID NO: 3.
2. A nucleic acid encoding the polypeptide of claim 1.
3. An isolated polypeptide comprising SEQ ID NO: 6.
4. A nucleic acid encoding the polypeptide of claim 3.
5. An isolated polypeptide comprising SEQ ID NO: 8.
6. A nucleic acid encoding the polypeptide of claim 5.

* * * * *

SEQUENCE LISTING (1) GENERAL INFORMATION:

(iii) NUMBER OF SEQUENCES: 43

(2) INFORMATION FOR SEQ ID NO:1:

(i) SEQUENCE CHARACTERISTICS:
      (A) LENGTH: 1844 base pairs
      (B) TYPE: nucleic acid
      (C) STRANDEDNESS: single
      (D) TOPOLOGY: linear (ix) FEATURE:
      (A) NAME/KEY: Coding Sequence
      (B) LOCATION: 104...1591
      (D) OTHER INFORMATION:

(xi) SEQUENCE DESCRIPTION: SEQ ID NO:1:

```
CTTGACGCCT GAGGGNCTGT AAGAACACGC CAGTCCCGCC GGCAGGCTGA TACGCGGCTG     60

CCGGCAGCCA GCGTCCGCAA GGGCGCACGC GGACCTGCAA AAC ATG CAT ACG AGC    115
                                                Met His Thr Ser
                                                 1

CGT CCG CGC GGC GTG CAC AGC ATC GCG CTA GTG CTG TCT CTC GCG ATT   163
Arg Pro Arg Gly Val His Ser Ile Ala Leu Val Leu Ser Leu Ala Ile
 5                  10                  15                  20

GCC TGG TTA CCT CAT GCT GAC CAT GCC GCG GGA GCG GGA GGA GGG GGG   211
Ala Trp Leu Pro His Ala Asp His Ala Ala Gly Ala Gly Gly Gly Gly
                 25                  30                  35

ATG TTT GGT GAC GTC AAT ATC TCA GCC ATT TTG GAT TCG CTA AGT GTA   259
Met Phe Gly Asp Val Asn Ile Ser Ala Ile Leu Asp Ser Leu Ser Val
                 40                  45                  50

AGC TAC GAC AAA AGA GTG AGG CCG AAC TAT GGA GGA CCG CCA GTG GAT   307
Ser Tyr Asp Lys Arg Val Arg Pro Asn Tyr Gly Gly Pro Pro Val Asp
         55                  60                  65

GTG GGA GTC ACC ATG TAC GTG CTC TCC ATC AGC TCC TTA TCT GAA GTG   355
Val Gly Val Thr Met Tyr Val Leu Ser Ile Ser Ser Leu Ser Glu Val
 70                  75                  80

AAA ATG GAT TTC ACC CTG GAT TTC TAC TTC AGA CAA TTT TGG ACA GAC   403
Lys Met Asp Phe Thr Leu Asp Phe Tyr Phe Arg Gln Phe Trp Thr Asp
 85                  90                  95                 100

CCC AGG CTT GCT TAC AAA AAA AGG ACG GGT GTG GAG ACT CTG TCC GTC   451
Pro Arg Leu Ala Tyr Lys Lys Arg Thr Gly Val Glu Thr Leu Ser Val
                105                 110                 115

GGC TCG GAA TTT ATT AGA AAC ATA TGG GTA CCC GAC ACC TTC TTT GTT   499
Gly Ser Glu Phe Ile Arg Asn Ile Trp Val Pro Asp Thr Phe Phe Val
                120                 125                 130

AAC GAA AAA CAG TCT TAT TTC CAC ATA GCT ACT ACA AGC AAC GAA TTC   547
Asn Glu Lys Gln Ser Tyr Phe His Ile Ala Thr Thr Ser Asn Glu Phe
                135                 140                 145
```

```
ATA CGC ATT CAT CAT TCT GGA TCT ATT ACT AGG AGT ATA AGA CTG ACT    595
Ile Arg Ile His His Ser Gly Ser Ile Thr Arg Ser Ile Arg Leu Thr
    150                 155                 160

ATC ACC GCT TCT TGT CCG ATG GAT TTG CAG TAT TTT CCG ATG GAC CGT    643
Ile Thr Ala Ser Cys Pro Met Asp Leu Gln Tyr Phe Pro Met Asp Arg
165                 170                 175                 180

CAA TTA TGC AAT ATT GAA ATC GAA AGT TTT GGC TAC ACC ATG CGG GAC    691
Gln Leu Cys Asn Ile Glu Ile Glu Ser Phe Gly Tyr Thr Met Arg Asp
                185                 190                 195

ATC CGA TAC AAG TGG AAT GAG GGG CCC AAC TCA GTG GGT GTG TCG AGC    739
Ile Arg Tyr Lys Trp Asn Glu Gly Pro Asn Ser Val Gly Val Ser Ser
                200                 205                 210

GAA GTG TCT TTG CCG CAA TTC AAG GTG CTG GGC CAC CGG CAG CGG GCC    787
Glu Val Ser Leu Pro Gln Phe Lys Val Leu Gly His Arg Gln Arg Ala
            215                 220                 225

ATG GAG ATT TCT CTT ACG ACA GGA AAC TAC TCT CGT CTG GCA TGT GAA    835
Met Glu Ile Ser Leu Thr Thr Gly Asn Tyr Ser Arg Leu Ala Cys Glu
    230                 235                 240

ATT CAA TTT GTA CGC TCG ATG GGA TAC TAT TTA ATT CAG ATT TAT ATT    883
Ile Gln Phe Val Arg Ser Met Gly Tyr Tyr Leu Ile Gln Ile Tyr Ile
245                 250                 255                 260

CCG TCT GGC CTA ATT GTC ATT ATA TCT TGG GTA TCA TTT TGG TTG AAT    931
Pro Ser Gly Leu Ile Val Ile Ile Ser Trp Val Ser Phe Trp Leu Asn
                265                 270                 275

CGA AAT GCG ACA CCT GCA AGG GTA TCA CTA GGT GTC ACA ACT GTA TTG    979
Arg Asn Ala Thr Pro Ala Arg Val Ser Leu Gly Val Thr Thr Val Leu
                280                 285                 290

ACG ATG ACG ACG CTC ATG TCG TCC ACG AAT GCG GCT CTG CCC AAG ATC   1027
Thr Met Thr Thr Leu Met Ser Ser Thr Asn Ala Ala Leu Pro Lys Ile
            295                 300                 305

TCA TAT GTC AAG TCC ATC GAT GTC TAT CTG GGA ACT TGT TTC GTC ATG   1075
Ser Tyr Val Lys Ser Ile Asp Val Tyr Leu Gly Thr Cys Phe Val Met
    310                 315                 320

GTC TTC GCC AGT TTA CTA GAA TAT GCC ACG GTT GGC TAT ATG GCT AAA   1123
Val Phe Ala Ser Leu Leu Glu Tyr Ala Thr Val Gly Tyr Met Ala Lys
325                 330                 335                 340

AGG ATA CAG ATG AGG AAA CAA AGA TTC ACT GCT GTT CAA AAA ATG GCC   1171
Arg Ile Gln Met Arg Lys Gln Arg Phe Thr Ala Val Gln Lys Met Ala
                345                 350                 355

GCC GAG AAG AAA ATG CAA ATA GAT GGT CCT CCA GGG TCA GCT GAG CCT   1219
Ala Glu Lys Lys Met Gln Ile Asp Gly Pro Pro Gly Ser Ala Glu Pro
                360                 365                 370

ATC CCC CCA CCG AGG ACC AGC ACC CTA TCT AGG CCA CCA CCA CCT AGC   1267
Ile Pro Pro Pro Arg Thr Ser Thr Leu Ser Arg Pro Pro Pro Pro Ser
            375                 380                 385

CGA TTA TCG GAG GTT CGG TTC AAA GTT CAC GAT CCG AAG GCA TAT TCT   1315
Arg Leu Ser Glu Val Arg Phe Lys Val His Asp Pro Lys Ala Tyr Ser
    390                 395                 400

AAA GGC GGT ACT TTA GAA AAC ACT ATC AAT GGG GCT CGG GGC CCA GCC   1363
Lys Gly Gly Thr Leu Glu Asn Thr Ile Asn Gly Ala Arg Gly Pro Ala
405                 410                 415                 420

CCA GGA CCT GCT CCA CCG GCA GAC GAA GAA GCT GGA CCA CCT CCG CAT   1411
Pro Gly Pro Ala Pro Pro Ala Asp Glu Glu Ala Gly Pro Pro Pro His
                425                 430                 435

CTC GTT CAT GCT TCC AAG GGT ATC AAC AAA CTG CTC GGC ACG ACC CCC   1459
Leu Val His Ala Ser Lys Gly Ile Asn Lys Leu Leu Gly Thr Thr Pro
                440                 445                 450

TCG GAC ATC GAC AAG TAC TCG CGC ATC GTG TTC CCC GTC TGC TTC GTT   1507
Ser Asp Ile Asp Lys Tyr Ser Arg Ile Val Phe Pro Val Cys Phe Val
```

```
                455                 460                 465
TGC TTT AAC CTT ATG TAC TGG ATC ATT TAC CTT CAC GTG TCT GAC GTC    1555
Cys Phe Asn Leu Met Tyr Trp Ile Ile Tyr Leu His Val Ser Asp Val
        470                 475                 480

GTG GCT GAT GAC TTG GTA CTA CTA GGC GAA GAA AAT TGAATTCTCT TTAACT  1607
Val Ala Asp Asp Leu Val Leu Leu Gly Glu Glu Asn
485                 490                 495

ATACCGGACT TGTTTTAACT TAGGGTGCTT ATGATCAACC ATCCATCAAG TTTCGGTAAA  1667

GTTCTTTAAA TCCTAGAAAC GCTCAGTAAA ATAATAGCGT TCTTTGTGTT TATAAATATA  1727

ATTATAGTAC AGATCACTAT GTTTATTATA GATAAGTGTC GTGTATATTG GCACTGGTAA  1787

TATTAATTCT TTAGAAAATA AAGATAATAT GAAGTTCAAA AAAAAAAAAA AAAAAA      1844
```

(2) INFORMATION FOR SEQ ID NO:2:

(i) SEQUENCE CHARACTERISTICS:
        (A) LENGTH: 496 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

```
Met His Thr Ser Arg Pro Arg Gly Val His Ser Ile Ala Leu Val Leu
1               5                   10                  15

Ser Leu Ala Ile Ala Trp Leu Pro His Ala Asp His Ala Ala Gly Ala
                20                  25                  30

Gly Gly Gly Gly Met Phe Gly Asp Val Asn Ile Ser Ala Ile Leu Asp
            35                  40                  45

Ser Leu Ser Val Ser Tyr Asp Lys Arg Val Arg Pro Asn Tyr Gly Gly
        50                  55                  60

Pro Pro Val Asp Val Gly Val Thr Met Tyr Val Leu Ser Ile Ser Ser
65                  70                  75                  80

Leu Ser Glu Val Lys Met Asp Phe Thr Leu Asp Phe Tyr Phe Arg Gln
                85                  90                  95

Phe Trp Thr Asp Pro Arg Leu Ala Tyr Lys Lys Arg Thr Gly Val Glu
            100                 105                 110

Thr Leu Ser Val Gly Ser Glu Phe Ile Arg Asn Ile Trp Val Pro Asp
        115                 120                 125

Thr Phe Phe Val Asn Glu Lys Gln Ser Tyr Phe His Ile Ala Thr Thr
130                 135                 140

Ser Asn Glu Phe Ile Arg Ile His His Ser Gly Ser Ile Thr Arg Ser
145                 150                 155                 160

Ile Arg Leu Thr Ile Thr Ala Ser Cys Pro Met Asp Leu Gln Tyr Phe
                165                 170                 175

Pro Met Asp Arg Gln Leu Cys Asn Ile Glu Ile Glu Ser Phe Gly Tyr
            180                 185                 190

Thr Met Arg Asp Ile Arg Tyr Lys Trp Asn Glu Gly Pro Asn Ser Val
        195                 200                 205

Gly Val Ser Ser Glu Val Ser Leu Pro Gln Phe Lys Val Leu Gly His
210                 215                 220

Arg Gln Arg Ala Met Glu Ile Ser Leu Thr Thr Gly Asn Tyr Ser Arg
225                 230                 235                 240

Leu Ala Cys Glu Ile Gln Phe Val Arg Ser Met Gly Tyr Tyr Leu Ile
```

```
                        245                 250                 255
Gln Ile Tyr Ile Pro Ser Gly Leu Ile Val Ile Ser Trp Val Ser
                260                 265                 270

Phe Trp Leu Asn Arg Asn Ala Thr Pro Ala Arg Val Ser Leu Gly Val
            275                 280                 285

Thr Thr Val Leu Thr Met Thr Thr Leu Met Ser Ser Thr Asn Ala Ala
        290                 295                 300

Leu Pro Lys Ile Ser Tyr Val Lys Ser Ile Asp Val Tyr Leu Gly Thr
305                 310                 315                 320

Cys Phe Val Met Val Phe Ala Ser Leu Leu Glu Tyr Ala Thr Val Gly
                325                 330                 335

Tyr Met Ala Lys Arg Ile Gln Met Arg Lys Gln Arg Phe Thr Ala Val
                340                 345                 350

Gln Lys Met Ala Ala Glu Lys Lys Met Gln Ile Asp Gly Pro Pro Gly
            355                 360                 365

Ser Ala Glu Pro Ile Pro Pro Arg Thr Ser Thr Leu Ser Arg Pro
        370                 375                 380

Pro Pro Pro Ser Arg Leu Ser Glu Val Arg Phe Lys Val His Asp Pro
385                 390                 395                 400

Lys Ala Tyr Ser Lys Gly Gly Thr Leu Glu Asn Thr Ile Asn Gly Ala
                405                 410                 415

Arg Gly Pro Ala Pro Gly Pro Ala Pro Ala Asp Glu Glu Ala Gly
            420                 425                 430

Pro Pro Pro His Leu Val His Ala Ser Lys Gly Ile Asn Lys Leu Leu
            435                 440                 445

Gly Thr Thr Pro Ser Asp Ile Asp Lys Tyr Ser Arg Ile Val Phe Pro
    450                 455                 460

Val Cys Phe Val Cys Phe Asn Leu Met Tyr Trp Ile Ile Tyr Leu His
465                 470                 475                 480

Val Ser Asp Val Val Ala Asp Asp Leu Val Leu Leu Gly Glu Glu Asn
                485                 490                 495

(2) INFORMATION FOR SEQ ID NO:3:

(i) SEQUENCE CHARACTERISTICS:
        (A) LENGTH: 467 amino acids
        (B) TYPE: amino acid
        (C) STRANDEDNESS: single
        (D) TOPOLOGY: linear (xi) SEQUENCE DESCRIPTION: SEQ ID NO:3:

Ala Gly Ala Gly Gly Gly Met Phe Gly Asp Val Asn Ile Ser Ala
1               5                   10                  15

Ile Leu Asp Ser Leu Ser Val Ser Tyr Asp Lys Arg Val Arg Pro Asn
                20                  25                  30

Tyr Gly Gly Pro Pro Val Asp Val Gly Val Thr Met Tyr Val Leu Ser
            35                  40                  45

Ile Ser Ser Leu Ser Glu Val Lys Met Asp Phe Thr Leu Asp Phe Tyr
    50                  55                  60

Phe Arg Gln Phe Trp Thr Asp Pro Arg Leu Ala Tyr Lys Lys Arg Thr
65                  70                  75                  80

Gly Val Glu Thr Leu Ser Val Gly Ser Glu Phe Ile Arg Asn Ile Trp
                85                  90                  95

Val Pro Asp Thr Phe Phe Val Asn Glu Lys Gln Ser Tyr Phe His Ile
                100                 105                 110
```

```
Ala Thr Thr Ser Asn Glu Phe Ile Arg Ile His His Ser Gly Ser Ile
        115                 120                 125

Thr Arg Ser Ile Arg Leu Thr Ile Thr Ala Ser Cys Pro Met Asp Leu
130                 135                 140

Gln Tyr Phe Pro Met Asp Arg Gln Leu Cys Asn Ile Glu Ile Glu Ser
145                 150                 155                 160

Phe Gly Tyr Thr Met Arg Asp Ile Arg Tyr Lys Trp Asn Glu Gly Pro
                165                 170                 175

Asn Ser Val Gly Val Ser Ser Glu Val Ser Leu Pro Gln Phe Lys Val
                180                 185                 190

Leu Gly His Arg Gln Arg Ala Met Glu Ile Ser Leu Thr Thr Gly Asn
                195                 200                 205

Tyr Ser Arg Leu Ala Cys Glu Ile Gln Phe Val Arg Ser Met Gly Tyr
        210                 215                 220

Tyr Leu Ile Gln Ile Tyr Ile Pro Ser Gly Leu Ile Val Ile Ile Ser
225                 230                 235                 240

Trp Val Ser Phe Trp Leu Asn Arg Asn Ala Thr Pro Ala Arg Val Ser
                245                 250                 255

Leu Gly Val Thr Thr Val Leu Thr Met Thr Thr Leu Met Ser Ser Thr
                260                 265                 270

Asn Ala Ala Leu Pro Lys Ile Ser Tyr Val Lys Ser Ile Asp Val Tyr
                275                 280                 285

Leu Gly Thr Cys Phe Val Met Val Phe Ala Ser Leu Leu Glu Tyr Ala
        290                 295                 300

Thr Val Gly Tyr Met Ala Lys Arg Ile Gln Met Arg Lys Gln Arg Phe
305                 310                 315                 320

Thr Ala Val Gln Lys Met Ala Ala Glu Lys Lys Met Gln Ile Asp Gly
                325                 330                 335

Pro Pro Gly Ser Ala Glu Pro Ile Pro Pro Arg Thr Ser Thr Leu
                340                 345                 350

Ser Arg Pro Pro Pro Ser Arg Leu Ser Glu Val Arg Phe Lys Val
        355                 360                 365

His Asp Pro Lys Ala Tyr Ser Lys Gly Gly Thr Leu Glu Asn Thr Ile
        370                 375                 380

Asn Gly Ala Arg Gly Pro Ala Pro Gly Pro Ala Pro Pro Ala Asp Glu
385                 390                 395                 400

Glu Ala Gly Pro Pro His Leu Val His Ala Ser Lys Gly Ile Asn
                405                 410                 415

Lys Leu Leu Gly Thr Thr Pro Ser Asp Ile Asp Lys Tyr Ser Arg Ile
                420                 425                 430

Val Phe Pro Val Cys Phe Val Cys Phe Asn Leu Met Tyr Trp Ile Ile
        435                 440                 445

Tyr Leu His Val Ser Asp Val Val Ala Asp Asp Leu Val Leu Leu Gly
        450                 455                 460

Glu Glu Asn
465

(2) INFORMATION FOR SEQ ID NO:4:

(i) SEQUENCE CHARACTERISTICS:
        (A) LENGTH: 1519 base pairs
        (B) TYPE: nucleic acid
        (C) STRANDEDNESS: single
        (D) TOPOLOGY: linear (ix) FEATURE:
```

(A) NAME/KEY: Coding Sequence
(B) LOCATION: 1...1443
(D) OTHER INFORMATION:

(xi) SEQUENCE DESCRIPTION: SEQ ID NO:4:

```
CGC CCC CGC TCC GCG CCG CTG CTG CTG GCG CTC GCG GCC GCC TTC CTA        48
Arg Pro Arg Ser Ala Pro Leu Leu Leu Ala Leu Ala Ala Ala Phe Leu
 1               5                  10                  15

CCG CAA GCC AAC CAT GTC GCG GGT GCC GGT GGG GGA GGG ATG TTC GGT        96
Pro Gln Ala Asn His Val Ala Gly Ala Gly Gly Gly Gly Met Phe Gly
                20                  25                  30

GAC GTC AAT ATA TCA GCC ATT TTG GAT TCA TTT AGT ATA AGT TAC GAC       144
Asp Val Asn Ile Ser Ala Ile Leu Asp Ser Phe Ser Ile Ser Tyr Asp
            35                  40                  45

AAA AGA GTA AGA CCA AAC TAT GGA GGT CCG CCA GTG GAG GTG GGC GTC       192
Lys Arg Val Arg Pro Asn Tyr Gly Gly Pro Pro Val Glu Val Gly Val
        50                  55                  60

ACC ATG TAT GTG CTC TCT ATC AGC TCC GTC TCC GAA GTG CTC ATG GAT       240
Thr Met Tyr Val Leu Ser Ile Ser Ser Val Ser Glu Val Leu Met Asp
65                  70                  75                  80

TTC ACA TTG GAC TTT TAC TTC AGA CAA TTT TGG ACT GAT CCT CGA TTA       288
Phe Thr Leu Asp Phe Tyr Phe Arg Gln Phe Trp Thr Asp Pro Arg Leu
                85                  90                  95

GCA TAC AAA AAA AGA ACC GGA GTT GAA ACT TTA TCT GTG GGC TCA GAA       336
Ala Tyr Lys Lys Arg Thr Gly Val Glu Thr Leu Ser Val Gly Ser Glu
            100                 105                 110

TTC ATA AAG AAC ATA TGG GTA CCC GAC ACG TTC TTT GTA AAT GAA AAG       384
Phe Ile Lys Asn Ile Trp Val Pro Asp Thr Phe Phe Val Asn Glu Lys
        115                 120                 125

CAA TCT TAT TTC CAT ATA GCA ACA ACC AGC AAT GAA TTC ATC CGT ATA       432
Gln Ser Tyr Phe His Ile Ala Thr Thr Ser Asn Glu Phe Ile Arg Ile
130                 135                 140

CAC TAT TCT GGC TCT ATC ACT AGA AGT ATC AGA TTG ACG ATC ACA GCC       480
His Tyr Ser Gly Ser Ile Thr Arg Ser Ile Arg Leu Thr Ile Thr Ala
145                 150                 155                 160

TCT TGC CCG ATG AAT TTG CAA TAC TTC CCG ATG GAT CGA CAG TTG TGC       528
Ser Cys Pro Met Asn Leu Gln Tyr Phe Pro Met Asp Arg Gln Leu Cys
                165                 170                 175

CAC ATA GAA ATT GAA AGT TTC GGC TAC ACC ATG CGG GAC ATC AGA TAC       576
His Ile Glu Ile Glu Ser Phe Gly Tyr Thr Met Arg Asp Ile Arg Tyr
            180                 185                 190

AAA TGG AAC GAA GGG CCC AAC TCT GTG GGT GTT TCC AGC GAA GTG TCG       624
Lys Trp Asn Glu Gly Pro Asn Ser Val Gly Val Ser Ser Glu Val Ser
        195                 200                 205

CTG CCG CAG TTC AAG GTG CTG GGT CAT CGC CAA CGA GCT ATG GAG ATC       672
Leu Pro Gln Phe Lys Val Leu Gly His Arg Gln Arg Ala Met Glu Ile
210                 215                 220

TCC CTT ACT ACA GGA AAT TAT TCA CGG TTG GCA TGT GAA ATA CAA TTC       720
Ser Leu Thr Thr Gly Asn Tyr Ser Arg Leu Ala Cys Glu Ile Gln Phe
225                 230                 235                 240

GTT CGG TCT ATG GGA TAT TAC TTA ATC CAA ATT TAT ATT CCC TCT GGT       768
Val Arg Ser Met Gly Tyr Tyr Leu Ile Gln Ile Tyr Ile Pro Ser Gly
                245                 250                 255

TTG ATT GTC ATC ATA TCA TGG GTA TCA TTT TGG TTG AAT CGA AAT GCC       816
Leu Ile Val Ile Ile Ser Trp Val Ser Phe Trp Leu Asn Arg Asn Ala
            260                 265                 270

ACA CCA GCT CGA GTG GCC CTA GGT GTT ACC ACT GTA TTG ACA ATG ACA       864
Thr Pro Ala Arg Val Ala Leu Gly Val Thr Thr Val Leu Thr Met Thr
        275                 280                 285

ACG CTT ATG TCG TCT ACT AAC GCG GCG CTG CCC AAG ATC TCA TAC GTC       912
```

```
                 Thr Leu Met Ser Ser Thr Asn Ala Ala Leu Pro Lys Ile Ser Tyr Val
                         290                 295                 300

AAA TCC ATA GAT GTA TAT CTG GGG ACA TGT TTC GTC ATG GTA TTC GCT              960
Lys Ser Ile Asp Val Tyr Leu Gly Thr Cys Phe Val Met Val Phe Ala
305                 310                 315                 320

AGT CTA CTA GAA TAC GCG ACT GTG GGA TAT ATG GCA AAG AGA ATA CAG             1008
Ser Leu Leu Glu Tyr Ala Thr Val Gly Tyr Met Ala Lys Arg Ile Gln
                325                 330                 335

ATG AGA AAA CAA AGA TTT GTG GCC ATA CAG AAA ATA GCT TCT GAA AAG             1056
Met Arg Lys Gln Arg Phe Val Ala Ile Gln Lys Ile Ala Ser Glu Lys
                340                 345                 350

AAA ATC CCC GTT GAC TGC CCA CCC GTA GGC GAT CCA CAT ACT TTA TCG             1104
Lys Ile Pro Val Asp Cys Pro Pro Val Gly Asp Pro His Thr Leu Ser
355                 360                 365

AAG ATG GGA ACA CTT GGC AGA TGC CCA CCC GGT AGA CCA TCG GAG GTG             1152
Lys Met Gly Thr Leu Gly Arg Cys Pro Pro Gly Arg Pro Ser Glu Val
    370                 375                 380

CGG TTC AAA GTG CAT GAC CCA AAA GCG CAT TCC AAA GGC GGG ACG TTA             1200
Arg Phe Lys Val His Asp Pro Lys Ala His Ser Lys Gly Gly Thr Leu
385                 390                 395                 400

GAG AAC ACT ATT AAT GGA GGT CGC AGT GGA GCA GAA GAA GAA AAC CCA             1248
Glu Asn Thr Ile Asn Gly Gly Arg Ser Gly Ala Glu Glu Glu Asn Pro
                405                 410                 415

GGC CCG CCC CCA CAC ATT TTA CAT CCC GGC AAG GAC ATA AGC AAA CTG             1296
Gly Pro Pro Pro His Ile Leu His Pro Gly Lys Asp Ile Ser Lys Leu
                420                 425                 430

CTC GGC ATG ACT CCC TCG GAC ATC GAC AAG TAC TCG CGC ATC GTG TTC             1344
Leu Gly Met Thr Pro Ser Asp Ile Asp Lys Tyr Ser Arg Ile Val Phe
            435                 440                 445

CCC GTC TGC TTC GTT TGC TTT AAC CTT ATG TAC TGG ATC ATT TAC CTT             1392
Pro Val Cys Phe Val Cys Phe Asn Leu Met Tyr Trp Ile Ile Tyr Leu
    450                 455                 460

CAC GTG TCT GAC GTC GTG GCT GAC GAT CTG GTT CTA CTG GAA GAG GAT             1440
His Val Ser Asp Val Val Ala Asp Asp Leu Val Leu Leu Glu Glu Asp
465                 470                 475                 480

AAA TAGAGGGCGC AGTACATAAT CCACTTATTT TCCACAWCTG CAAGCTAAAT AATAAT          1499
Lys

TTGAAACGGA TAAAACTTTA                                                      1519

(2) INFORMATION FOR SEQ ID NO:5:

(i) SEQUENCE CHARACTERISTICS:
        (A) LENGTH: 481 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:5:

Arg Pro Arg Ser Ala Pro Leu Leu Leu Ala Leu Ala Ala Ala Phe Leu
1               5                   10                  15

Pro Gln Ala Asn His Val Ala Gly Ala Gly Gly Gly Met Phe Gly
            20                  25                  30

Asp Val Asn Ile Ser Ala Ile Leu Asp Ser Phe Ser Ile Ser Tyr Asp
                35                  40                  45

Lys Arg Val Arg Pro Asn Tyr Gly Gly Pro Pro Val Glu Val Gly Val
        50                  55                  60
```

```
Thr Met Tyr Val Leu Ser Ile Ser Val Ser Glu Val Leu Met Asp
 65                  70                  75                  80

Phe Thr Leu Asp Phe Tyr Phe Arg Gln Phe Trp Thr Asp Pro Arg Leu
                 85                  90                  95

Ala Tyr Lys Lys Arg Thr Gly Val Glu Thr Leu Ser Val Gly Ser Glu
            100                 105                 110

Phe Ile Lys Asn Ile Trp Val Pro Asp Thr Phe Phe Val Asn Glu Lys
            115                 120                 125

Gln Ser Tyr Phe His Ile Ala Thr Thr Ser Asn Glu Phe Ile Arg Ile
            130                 135                 140

His Tyr Ser Gly Ser Ile Thr Arg Ser Ile Arg Leu Thr Ile Thr Ala
145                 150                 155                 160

Ser Cys Pro Met Asn Leu Gln Tyr Phe Pro Met Asp Arg Gln Leu Cys
                165                 170                 175

His Ile Glu Ile Glu Ser Phe Gly Tyr Thr Met Arg Asp Ile Arg Tyr
            180                 185                 190

Lys Trp Asn Glu Gly Pro Asn Ser Val Gly Val Ser Ser Glu Val Ser
            195                 200                 205

Leu Pro Gln Phe Lys Val Leu Gly His Arg Gln Arg Ala Met Glu Ile
    210                 215                 220

Ser Leu Thr Thr Gly Asn Tyr Ser Arg Leu Ala Cys Glu Ile Gln Phe
225                 230                 235                 240

Val Arg Ser Met Gly Tyr Tyr Leu Ile Gln Ile Tyr Ile Pro Ser Gly
                245                 250                 255

Leu Ile Val Ile Ile Ser Trp Val Ser Phe Trp Leu Asn Arg Asn Ala
            260                 265                 270

Thr Pro Ala Arg Val Ala Leu Gly Val Thr Thr Val Leu Thr Met Thr
            275                 280                 285

Thr Leu Met Ser Ser Thr Asn Ala Ala Leu Pro Lys Ile Ser Tyr Val
    290                 295                 300

Lys Ser Ile Asp Val Tyr Leu Gly Thr Cys Phe Val Met Val Phe Ala
305                 310                 315                 320

Ser Leu Leu Glu Tyr Ala Thr Val Gly Tyr Met Ala Lys Arg Ile Gln
                325                 330                 335

Met Arg Lys Gln Arg Phe Val Ala Ile Gln Lys Ile Ala Ser Glu Lys
            340                 345                 350

Lys Ile Pro Val Asp Cys Pro Pro Val Gly Asp Pro His Thr Leu Ser
            355                 360                 365

Lys Met Gly Thr Leu Gly Arg Cys Pro Pro Gly Arg Pro Ser Glu Val
    370                 375                 380

Arg Phe Lys Val His Asp Pro Lys Ala His Ser Lys Gly Gly Thr Leu
385                 390                 395                 400

Glu Asn Thr Ile Asn Gly Gly Arg Ser Gly Ala Glu Glu Asn Pro
                405                 410                 415

Gly Pro Pro His Ile Leu His Pro Gly Lys Asp Ile Ser Lys Leu
            420                 425                 430

Leu Gly Met Thr Pro Ser Asp Ile Asp Lys Tyr Ser Arg Ile Val Phe
            435                 440                 445

Pro Val Cys Phe Val Cys Phe Asn Leu Met Tyr Trp Ile Ile Tyr Leu
    450                 455                 460

His Val Ser Asp Val Val Ala Asp Asp Leu Val Leu Leu Glu Glu Asp
465                 470                 475                 480

Lys
```

(2) INFORMATION FOR SEQ ID NO:6:

(i) SEQUENCE CHARACTERISTICS:
        (A) LENGTH: 459 amino acids
        (B) TYPE: amino acid
        (C) STRANDEDNESS: single
        (D) TOPOLOGY: linear (xi) SEQUENCE DESCRIPTION: SEQ ID NO:6:

```
Ala Gly Ala Gly Gly Gly Met Phe Gly Asp Val Asn Ile Ser Ala
 1               5                  10                  15

Ile Leu Asp Ser Phe Ser Ile Ser Tyr Asp Lys Arg Val Arg Pro Asn
            20                  25                  30

Tyr Gly Gly Pro Pro Val Glu Val Gly Val Thr Met Tyr Val Leu Ser
         35                  40                  45

Ile Ser Ser Val Ser Glu Val Leu Met Asp Phe Thr Leu Asp Phe Tyr
 50                  55                  60

Phe Arg Gln Phe Trp Thr Asp Pro Arg Leu Ala Tyr Lys Lys Arg Thr
 65                  70                  75                  80

Gly Val Glu Thr Leu Ser Val Gly Ser Glu Phe Ile Lys Asn Ile Trp
                 85                  90                  95

Val Pro Asp Thr Phe Phe Val Asn Glu Lys Gln Ser Tyr Phe His Ile
                100                 105                 110

Ala Thr Thr Ser Asn Glu Phe Ile Arg Ile His Tyr Ser Gly Ser Ile
             115                 120                 125

Thr Arg Ser Ile Arg Leu Thr Ile Thr Ala Ser Cys Pro Met Asn Leu
         130                 135                 140

Gln Tyr Phe Pro Met Asp Arg Gln Leu Cys His Ile Glu Ile Glu Ser
145                 150                 155                 160

Phe Gly Tyr Thr Met Arg Asp Ile Arg Tyr Lys Trp Asn Glu Gly Pro
                165                 170                 175

Asn Ser Val Gly Val Ser Ser Glu Val Ser Leu Pro Gln Phe Lys Val
            180                 185                 190

Leu Gly His Arg Gln Arg Ala Met Glu Ile Ser Leu Thr Thr Gly Asn
        195                 200                 205

Tyr Ser Arg Leu Ala Cys Glu Ile Gln Phe Val Arg Ser Met Gly Tyr
    210                 215                 220

Tyr Leu Ile Gln Ile Tyr Ile Pro Ser Gly Leu Ile Val Ile Ile Ser
225                 230                 235                 240

Trp Val Ser Phe Trp Leu Asn Arg Asn Ala Thr Pro Ala Arg Val Ala
                245                 250                 255

Leu Gly Val Thr Thr Val Leu Thr Met Thr Thr Leu Met Ser Ser Thr
            260                 265                 270

Asn Ala Ala Leu Pro Lys Ile Ser Tyr Val Lys Ser Ile Asp Val Tyr
        275                 280                 285

Leu Gly Thr Cys Phe Val Met Val Phe Ala Ser Leu Leu Glu Tyr Ala
    290                 295                 300

Thr Val Gly Tyr Met Ala Lys Arg Ile Gln Met Arg Lys Gln Arg Phe
305                 310                 315                 320

Val Ala Ile Gln Lys Ile Ala Ser Glu Lys Ile Pro Val Asp Cys
                325                 330                 335

Pro Pro Val Gly Asp Pro His Thr Leu Ser Lys Met Gly Thr Leu Gly
            340                 345                 350

Arg Cys Pro Pro Gly Arg Pro Ser Glu Val Arg Phe Lys Val His Asp
```

```
                  355                 360                 365
        Pro Lys Ala His Ser Lys Gly Gly Thr Leu Glu Asn Thr Ile Asn Gly
            370                 375                 380

Gly Arg Ser Gly Ala Glu Glu Asn Pro Gly Pro Pro His Ile
        385                 390                 395                 400

Leu His Pro Gly Lys Asp Ile Ser Lys Leu Leu Gly Met Thr Pro Ser
                        405                 410                 415

Asp Ile Asp Lys Tyr Ser Arg Ile Val Phe Pro Val Cys Phe Val Cys
                        420                 425                 430

Phe Asn Leu Met Tyr Trp Ile Ile Tyr Leu His Val Ser Asp Val Val
                        435                 440                 445

Ala Asp Asp Leu Val Leu Leu Glu Glu Asp Lys
            450                 455

(2) INFORMATION FOR SEQ ID NO:7:

(i) SEQUENCE CHARACTERISTICS:
          (A) LENGTH: 669 base pairs
          (B) TYPE: nucleic acid
          (C) STRANDEDNESS: single
          (D) TOPOLOGY: linear (ix) FEATURE:
          (A) NAME/KEY: Coding Sequence
          (B) LOCATION: 2...667
          (D) OTHER INFORMATION:

(xi) SEQUENCE DESCRIPTION: SEQ ID NO:7:

C TTC GTG AAC GAA AAG CAA TCG TAC TTC CAC ACG GCC ACC ACC AGT AAT     49
  Phe Val Asn Glu Lys Gln Ser Tyr Phe His Thr Ala Thr Thr Ser Asn
  1               5                   10                  15

GAG TTC ATC CGC ATC CAC CAC TCG GGC TCC ATC ACG CGT AGC ATA AGG       97
Glu Phe Ile Arg Ile His His Ser Gly Ser Ile Thr Arg Ser Ile Arg
                20                  25                  30

CTC ACC ATC ACG GCC TCC TGC CCC ATG AAC CTG CAG TAC TTC CCC ATG      145
Leu Thr Ile Thr Ala Ser Cys Pro Met Asn Leu Gln Tyr Phe Pro Met
                35                  40                  45

GAT CGG CAG CTG TGC CAC ATC GAG ATC GAG AGT TTC GGC TAC ACC ATG      193
Asp Arg Gln Leu Cys His Ile Glu Ile Glu Ser Phe Gly Tyr Thr Met
 50                  55                  60

CGG GAC ATC CGG TAC AAA TGG AAC GAG GGG NCC AAC TCG GTG GGC GTT      241
Arg Asp Ile Arg Tyr Lys Trp Asn Glu Gly Xaa Asn Ser Val Gly Val
 65                  70                  75                  80

TCA AAC GAA GTG TCG CTA CCG CAG TTC AAG GTG TTG GGC CAT CGT CAA      289
Ser Asn Glu Val Ser Leu Pro Gln Phe Lys Val Leu Gly His Arg Gln
                85                  90                  95

CGT GCC ATG GAA ATA TCG CTC ACA ACA GGA AAC TAC TCC CGG CTG GCG      337
Arg Ala Met Glu Ile Ser Leu Thr Thr Gly Asn Tyr Ser Arg Leu Ala
                100                 105                 110

TGC GAG ATC CAG TTC GTG CGC TCG ATG GGC TAC TAC CTG ATC CAG ATC      385
Cys Glu Ile Gln Phe Val Arg Ser Met Gly Tyr Tyr Leu Ile Gln Ile
                115                 120                 125

TAC ATA CCA TCC GGC CTC ATC GTC ATA ATA TCG TGG GTG TCT TTC TGG      433
Tyr Ile Pro Ser Gly Leu Ile Val Ile Ile Ser Trp Val Ser Phe Trp
                130                 135                 140

TTG AAC CGC AAC GCG ACG CCG GCG CGC GTG CAG CTG GGC GTC ACC ACC      481
Leu Asn Arg Asn Ala Thr Pro Ala Arg Val Gln Leu Gly Val Thr Thr
145                 150                 155                 160

GTG CTC ACC ATG ACC ACG CTC ATG TCT TCC ACT AAT GCG GCG CTG CCG      529
Val Leu Thr Met Thr Thr Leu Met Ser Ser Thr Asn Ala Ala Leu Pro
                165                 170                 175
```

```
AAG ATC TCG TAC GTT AAG TCC ATC GAT GTG TAC CTC GGC ACC TGC TTC        577
Lys Ile Ser Tyr Val Lys Ser Ile Asp Val Tyr Leu Gly Thr Cys Phe
            180                 185                 190

GTT ATG GTG TTC ACC AGT CTG CTA GAG TAC GCG ACG GTG GGG TAT ATG        625
Val Met Val Phe Thr Ser Leu Leu Glu Tyr Ala Thr Val Gly Tyr Met
        195                 200                 205

TCG AAG AGA ATA CAG ATG AGA AAG CAG CGC TTT GTC GCG ATC CC             669
Ser Lys Arg Ile Gln Met Arg Lys Gln Arg Phe Val Ala Ile
    210                 215                 220
```

(2) INFORMATION FOR SEQ ID NO:8:

(i) SEQUENCE CHARACTERISTICS:
        (A) LENGTH: 222 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:8:

```
Phe Val Asn Glu Lys Gln Ser Tyr Phe His Thr Ala Thr Thr Ser Asn
 1               5                  10                  15

Glu Phe Ile Arg Ile His His Ser Gly Ser Ile Thr Arg Ser Ile Arg
            20                  25                  30

Leu Thr Ile Thr Ala Ser Cys Pro Met Asn Leu Gln Tyr Phe Pro Met
        35                  40                  45

Asp Arg Gln Leu Cys His Ile Glu Ile Glu Ser Phe Gly Tyr Thr Met
    50                  55                  60

Arg Asp Ile Arg Tyr Lys Trp Asn Glu Gly Xaa Asn Ser Val Gly Val
65                  70                  75                  80

Ser Asn Glu Val Ser Leu Pro Gln Phe Lys Val Leu Gly His Arg Gln
                85                  90                  95

Arg Ala Met Glu Ile Ser Leu Thr Thr Gly Asn Tyr Ser Arg Leu Ala
            100                 105                 110

Cys Glu Ile Gln Phe Val Arg Ser Met Gly Tyr Tyr Leu Ile Gln Ile
        115                 120                 125

Tyr Ile Pro Ser Gly Leu Ile Val Ile Ser Trp Val Ser Phe Trp
    130                 135                 140

Leu Asn Arg Asn Ala Thr Pro Ala Arg Val Gln Leu Gly Val Thr Thr
145                 150                 155                 160

Val Leu Thr Met Thr Thr Leu Met Ser Ser Thr Asn Ala Ala Leu Pro
                165                 170                 175

Lys Ile Ser Tyr Val Lys Ser Ile Asp Val Tyr Leu Gly Thr Cys Phe
            180                 185                 190

Val Met Val Phe Thr Ser Leu Leu Glu Tyr Ala Thr Val Gly Tyr Met
        195                 200                 205

Ser Lys Arg Ile Gln Met Arg Lys Gln Arg Phe Val Ala Ile
    210                 215                 220
```

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:9:

GCRAANACCA TNACRAARCA                                              20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:10:

GTNGTCATNG TSAGNACNGT                                              20

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:11:

TGGGTNCCNG AYACNNT                                                 17

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:12:

CCGAGCTCSW RTAYTTRTCD ATRTC                                        25

(2) INFORMATION FOR SEQ ID NO:13:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:13:

CCGAGCTCAR RTADATDATC CARTACAT                                     28

(2) INFORMATION FOR SEQ ID NO:14:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:14:

AGGCGGCCGC GGNGTNACNA TGTAYGT                                      27

(2) INFORMATION FOR SEQ ID NO:15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:15:

```
CTGCGGCCGC CARTTYTGGA CNGAYCC                                           27
```

(2) INFORMATION FOR SEQ ID NO:16:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:16:

```
AATCTAGAGG GTGTCTTTCT GGTTG                                             25
```

(2) INFORMATION FOR SEQ ID NO:17:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:17:

```
AGCTCGAGAG TTTCGGCTAC ACCAT                                             25
```

(2) INFORMATION FOR SEQ ID NO:18:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:18:

```
TTCTCGAGCG ATGGATTTGC ACTATTTTC                                         29
```

(2) INFORMATION FOR SEQ ID NO:19:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:19:

```
CAGAGCTCAT TTCACATGCC AGACGAGAG                                         29
```

(2) INFORMATION FOR SEQ ID NO:20:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:20:

```
TAGAGCTCGA ATGATGAATG CGTATGAAT                                         29
```

(2) INFORMATION FOR SEQ ID NO:21:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:21:

```
TCTCTAGATA CGCTCGATGG GATAC                                          25

(2) INFORMATION FOR SEQ ID NO:22:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (xi) SEQUENCE DESCRIPTION: SEQ ID NO:22:

TTGCGGCCGC CATATATCCC ACAG                                           24

(2) INFORMATION FOR SEQ ID NO:23:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (xi) SEQUENCE DESCRIPTION: SEQ ID NO:23:

CTGCGGCCGC TCGAGCTGGT G                                              21

(2) INFORMATION FOR SEQ ID NO:24:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (xi) SEQUENCE DESCRIPTION: SEQ ID NO:24:

CGGATGAATT CATTGCTGGT TGTT                                           24

(2) INFORMATION FOR SEQ ID NO:25:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (xi) SEQUENCE DESCRIPTION: SEQ ID NO:25:

CTGTCGATCC ATCGGGAAGT ATTG                                           24

(2) INFORMATION FOR SEQ ID NO:26:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (xi) SEQUENCE DESCRIPTION: SEQ ID NO:26:

GCGGACCTCC ATAGTTTGGT C                                              21

(2) INFORMATION FOR SEQ ID NO:27:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (xi) SEQUENCE DESCRIPTION: SEQ ID NO:27:

CAGACGAAGA AGCTGGACCA CCTC                                           24
```

(2) INFORMATION FOR SEQ ID NO:28:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:28:

ACGCGGCCGC AAGGACATAA GCAA                          24

(2) INFORMATION FOR SEQ ID NO:29:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:29:

TTCTCGAGCG ATGGATTTGC ACTATTTTC                    29

(2) INFORMATION FOR SEQ ID NO:30:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:30:

AGTCCCGGCG GCAGGCTGAT A                            21

(2) INFORMATION FOR SEQ ID NO:31:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:31:

ATGACAATTA GGCCAGACGG AATA                         24

(2) INFORMATION FOR SEQ ID NO:32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:32:

CATCCGATAC AAGTGGAATG                              20

(2) INFORMATION FOR SEQ ID NO:33:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:33:

GTCGACCCAG TGCCAATATA CACGAC                      26

(2) INFORMATION FOR SEQ ID NO:34:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:34:

GTCGACTTAC CGAAACTTGA TGGATG                                      26

(2) INFORMATION FOR SEQ ID NO:35:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:35:

TTGCGGCCGC CATATATCCC ACAG                                        24

(2) INFORMATION FOR SEQ ID NO:36:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:36:

GTGAAATACA ATTCGTTCGG TCTA                                        24

(2) INFORMATION FOR SEQ ID NO:37:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:37:

GCAGATGTGG AAAATAAGTG GATT                                        24

(2) INFORMATION FOR SEQ ID NO:38:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:38:

AGCGAATACC ATGACGAAAC A                                            21

(2) INFORMATION FOR SEQ ID NO:39:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:39:

GCGGCCGCCT TCCTAC                                                        16

(2) INFORMATION FOR SEQ ID NO:40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:40:

ACCATCCATT TAGACGACGC          20

(2) INFORMATION FOR SEQ ID NO:41:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:41:

GTAACACCAA CTTCCACCG          19

(2) INFORMATION FOR SEQ ID NO:42:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:42:

GAATGGCCAA CATGTCGCTG GAAATC          26

(2) INFORMATION FOR SEQ ID NO:43:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:43:

AATAATGACG TCACCGAACA TCCCTCCCCC ACCG          34